United States Patent
Scherrer et al.

(10) Patent No.: US 10,806,729 B2
(45) Date of Patent: Oct. 20, 2020

(54) QUINOLINE DERIVATIVES FOR USE IN THE TREATMENT OR PREVENTION OF VIRAL INFECTION

(71) Applicants: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

(72) Inventors: Didier Scherrer, Castelnau le Lez (FR); Aude Garcel, Le Cres (FR); Noelie Campos, Le Cres (FR); Jamal Tazi, Clapiers (FR); Audrey Vautrin, Castelnau le Lez (FR); Florence Mahuteau, Saint Remy les Chevreuses (FR); Romain Najman, L'Hay-les-Roses (FR); Pauline Fornarelli, Villebon sur Yvette (FR)

(73) Assignees: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

( * ) Notice: Subject to any disclaimer, the term of this patent is extended or adjusted under 35 U.S.C. 154(b) by 119 days.

(21) Appl. No.: 15/552,921

(22) PCT Filed: Feb. 19, 2016

(86) PCT No.: PCT/EP2016/053535
§ 371 (c)(1),
(2) Date: Aug. 23, 2017

(87) PCT Pub. No.: WO2016/135055
PCT Pub. Date: Sep. 1, 2016

(65) Prior Publication Data
US 2018/0028522 A1    Feb. 1, 2018

(30) Foreign Application Priority Data
Feb. 23, 2015  (EP) ..................... 15305277

(51) Int. Cl.
*A61K 31/47*     (2006.01)
*A61K 31/4709*   (2006.01)
*A61K 31/706*    (2006.01)

(52) U.S. Cl.
CPC .......... *A61K 31/47* (2013.01); *A61K 31/4709* (2013.01); *A61K 31/706* (2013.01)

(58) Field of Classification Search
None
See application file for complete search history.

(56) References Cited

U.S. PATENT DOCUMENTS

| | | | | |
|---|---|---|---|---|
| 9,145,367 B2 * | 9/2015 | Tazi | ..................... | C07D 213/74 |
| 9,908,869 B2 * | 3/2018 | Tazi | ..................... | C07D 213/74 |

FOREIGN PATENT DOCUMENTS

| | | | |
|---|---|---|---|
| EP | 2465502 A1 | 6/2012 | |
| EP | 2757161 A1 | 7/2014 | |
| EP | 2974729 A1 | 1/2016 | |
| EP | 2975034 A1 | 1/2016 | |
| WO | 2010/143169 A2 | 12/2010 | |
| WO | WO-2010143169 A2 * | 12/2010 | ........... C07D 213/74 |

(Continued)

OTHER PUBLICATIONS

International Search Report for PCT/EP2016/053535 dated Apr. 29, 2016 (7 pages).

(Continued)

*Primary Examiner* — Traviss C McIntosh, III
(74) *Attorney, Agent, or Firm* — Oliff PLC

(57) ABSTRACT

The present invention relates to a quinoline derivative of formula (I) or anyone of its pharmaceutically acceptable salt, or anyone of its metabolites, for use for treating or preventing a viral infection, in particular a HIV infection or a HIV-related condition in a patient; and then terminating said treatment when: the viral load is low or undetectable; and/or the level of CD4+ cell count is maintained or restored. The present invention further relates to a quinoline derivative of formula (I) as defined in claim 1, or anyone of its pharmaceutically acceptable salts and metabolites, for use for treating or preventing a viral infection, in particular a HIV infection or a HIV-related condition in a patient, for which an ineffectiveness or a decline in a prior anti-retroviral treatment effectiveness has been stated and to a quinoline derivative of formula (I) as defined above, or anyone of its pharmaceutically acceptable salts and metabolites, for use for treating or preventing a viral infection, in particular a HIV infection or a HIV-related condition in a patient, wherein the patient is infected by a drug-resistant viral strain, and more particularly by a drug-resistant HIV strain.

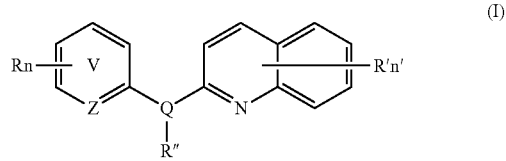

(I)

15 Claims, 5 Drawing Sheets

(56) References Cited

FOREIGN PATENT DOCUMENTS

| WO | 2012/080953 A1 | 6/2012 |
|---|---|---|
| WO | 2015/001518 A1 | 1/2015 |

OTHER PUBLICATIONS

Written Opinion for PCT/EP2016/053535 dated Apr. 29, 2016 (9 pages).
Bakkour et al., "Small-Molecule Inhibition of HIV pre-mRNA Splicing as a Novel Antiretroviral Therapy to Overcome Drug Resistance", PLoS Pathogens, vol. 3, No. 10, Oct. 2007, pp. 1530-1539.
Berges et al., "The utility of the new generation of humanized mice to study HIV-1 infection: transmission, prevention, pathogenesis, and treatment", Retrovirology 2011, vol. 8, No. 65, pp. 1-19.
Denton et al., "Humanized Mouse Models of HIV Infection", AIDS Rev., 2011, vol. 13, No. 3, pp. 135-148.
Iyidogan et al., "Current Perspective on HIV-1 Antiretroviral Drug Resistance", Viruses, 2014, vol. 6, pp. 4095-4139.
Klinck et al., "Multiple Alternative Splicing Markers for Ovarian Cancer", Cancer Res., 2008, vol. 63, No. 3, pp. 657-663; www.aacrjournals.org.
McDougal et al., "Immunoassay for the Detection and Quantitation of Infectious Human Retrovirus, Lymphadenopathy-Associated Virus (LAV)", Journal of Immunological Methods, 1985, vol. 76, pp. 171-183.
Nischang et al., "Humanized Mice Recapitulate Key Features of HIV-1 Infection: A Novel Concept Using Long-Acting Anti-Retroviral Drugs for Treating HIV-1", PLoS ONE, vol. 7, No. 6, Jun. 2012.
Venables et al., "Cancer-associated regulation of alternative splicing", Nature Structural & Molecular Biology, vol. 16, No. 6, Jun. 2009, pp. 670-881.
Wu et at., "Fast and SNP-tolerant detection of complex variants and splicing in short reads", Bioinformatics, vol. 26, No. 7, 2010, pp. 873-881.

\* cited by examiner

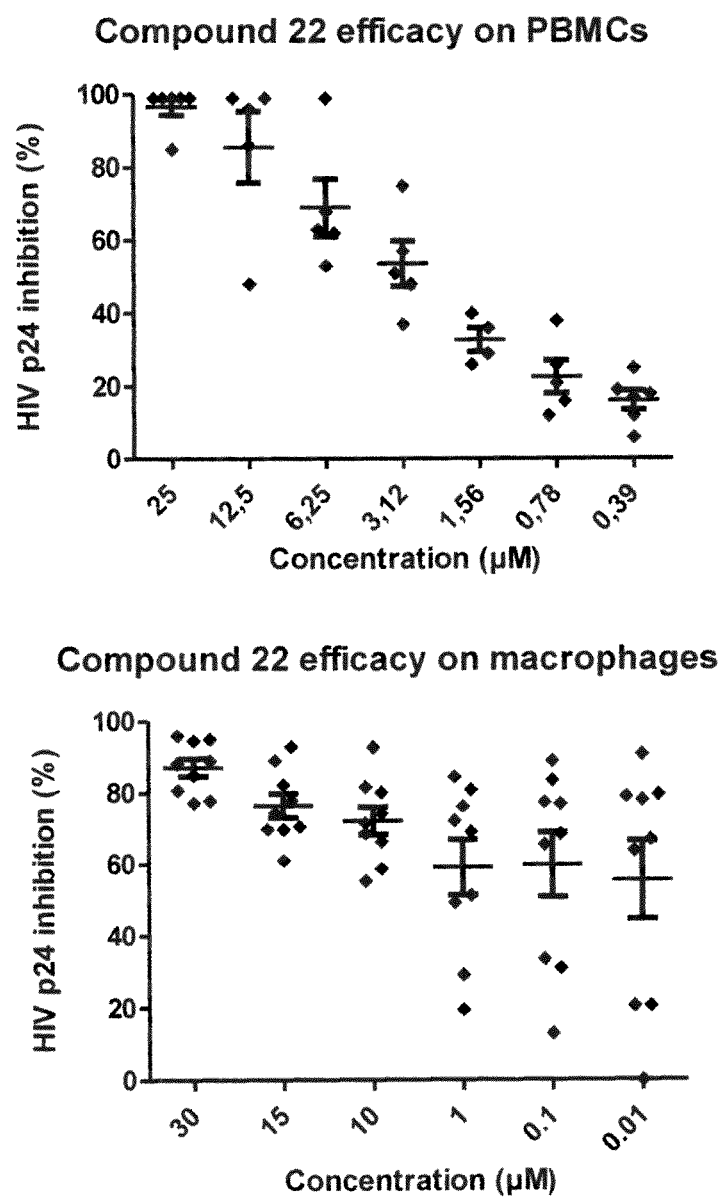
Figure 1A, B

| Virus strain | | % inhibition with Compound 22 |
|---|---|---|
| HIV-1 B subtype | Ad8 | 71 ± 4 |
| | AdaM | 99 ± 1 |
| | Isolate B | 83 ± 8 |
| HIV-1 C subtype | Isolate C | 89 ± 1 |
| HIV-1 recombinants | CRF01 | 82 ± 11 |
| | CRF02 | 86 ± 3 |
| | CRF06 | 80 ± 5 |
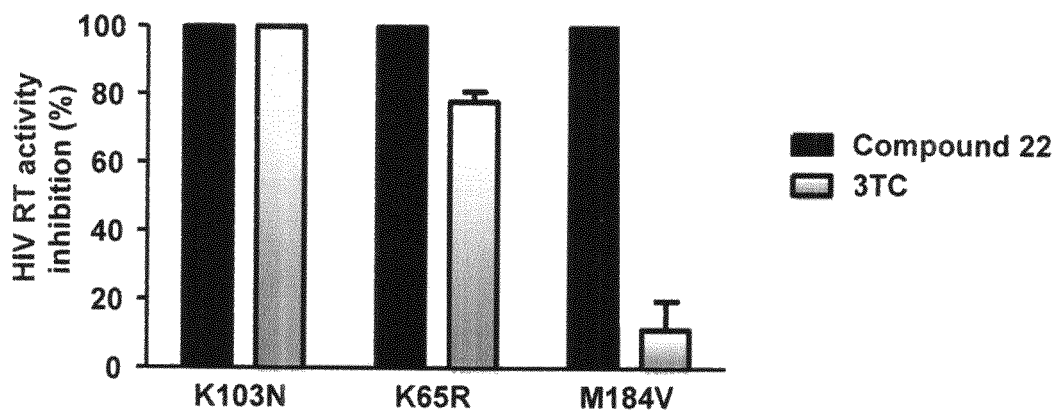
Figure 2A, B

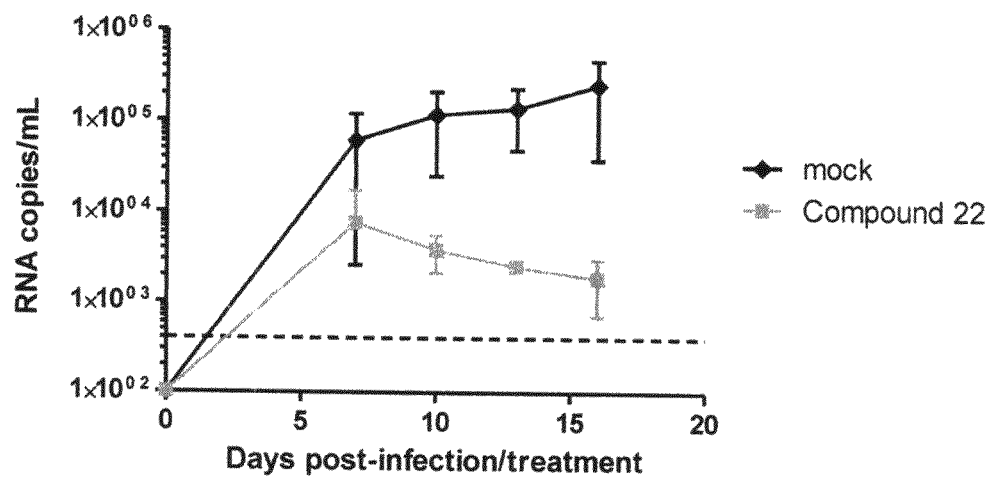
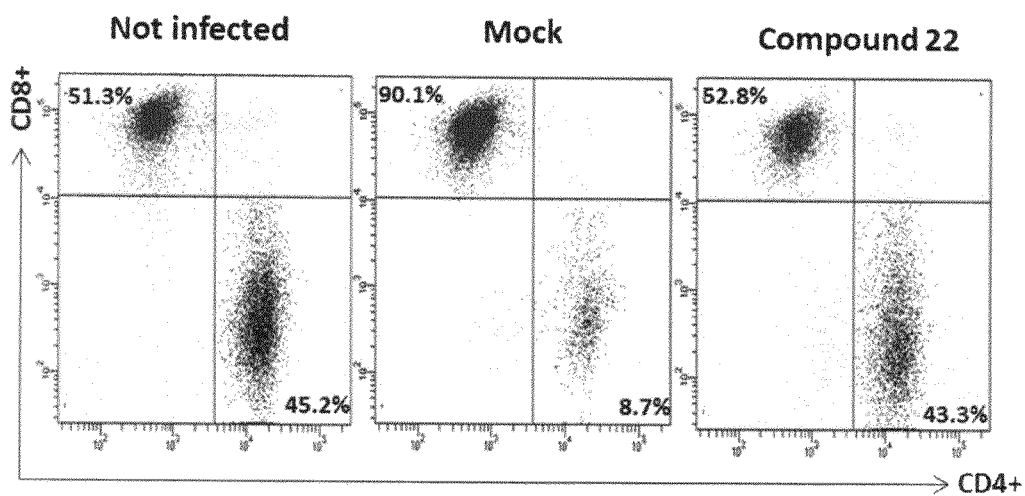
Figure 3A, B

QUINOLINE DERIVATIVES FOR USE IN THE TREATMENT OR PREVENTION OF VIRAL INFECTION

FIELD OF THE INVENTION

The present invention has for purpose to lower a viral load in a patient infected by a virus, in particular HIV, or a virus-related condition, with a long-lasting effect and absence of resistance.

The invention further relates to new doses and regimens of said quinoline derivatives and use in the treatment or prevention of viral infection, and in particular HIV, or a virus-related condition, more particularly where the use maintains a low viral load after treatment termination.

The invention also relates to the identification of quinoline derivatives which are efficient in the treatment or prevention of patients infected by a virus, in particular HIV, or a virus-related condition, for which an ineffectiveness or decline in a prior anti-HIV treatment effectiveness has been stated.

The invention also relates to the identification of quinoline derivatives which are efficient in the treatment or prevention of patients infected by viruses, in particular HIV, that are resistant to classical antiviral drugs.

BACKGROUND OF THE INVENTION

Viral replication relates to the formation of viruses during the infection process in the target host cells, including translation of viral RNAs by the endogenous machinery.

The identification of compounds for treating or preventing a viral infection or a virus-related condition in a patient has led to the development of novel therapies.

One of the drawbacks of current treatments of viral infections, and in particular HIV infections, is that viruses start multiplying again as soon as the drugs are withdrawn, which typically means daily, life-long treatment for patients.

Among virus-related conditions, AIDS has developed into a worldwide pandemic. More than 30 million people are infected with Human Immunodeficiency Virus (HIV). Current therapies have succeeded in controlling the disease but long-term use of Anti-Retroviral Therapy (ART) is limited due to the nature of the viral replication cycle of those viruses, but also by issues of side effects.

What is more, those compounds do not necessarily inhibit the replication of viral strains harbouring mutations in the long-term, which is prone to confer the development of drug-resistant strains and which also participates in the rebound of viral infection in otherwise treated patients.

In particular, for HIV infections, the current ART drugs need to be taken for life and only attenuate the disease without curing it. One reason is that current Human Immunodeficiency Virus (HIV) therapies reduce viral load during treatment but titers rebound after treatment is discontinued, which is one of the consequences of virus latency.

Alternatives to ART, including a combination 3TC-Tenofovir-Raltegravir and AZT (HAART), have thus been proposed.

Access to Highly Active Anti-Retroviral Therapy (HAART), based upon the combination of HIV protease and reverse transcriptase inhibitors, has dramatically changed the prognosis of HIV infection. As a result, HIV is considered as a chronic disease in developed countries. However, long-term use of HAART is limited by issues of drug resistance and side effects.

For example, resistance to new classes of anti-HIV/AIDS drugs such as Raltegravir® (integrase inhibitor) and Enfuvirtide® (entry inhibitor) has already been observed.

The reasons which explain the rebound of viral infections in previously-treated patients include:

(i) the fact that many viruses, including retroviruses such as HIV or DNA viruses of the Herpesviridae family, are characterized by viral latency, which is the ability of a virus to lie dormant within a cell, thus defining the lysogenic part of the viral life cycle. Latency is the phase of the viral replication cycle in which, after initial infection, proliferation of virus particles ceases without full eradication. The phenomenon of viral latency is associated to the appearance of so-called "reservoirs" within the host, which are generally difficult to reach, and which are also one of the main reasons of the difficulty to provide a cure for HIV;

(ii) the emergence of drug-resistant strains, especially for viral infections requiring a long-term treatment. The probability of appearance of mutant strains is particularly important for retroviruses, including HIV. Indeed, resistance to anti-HIV drugs can be explained at the biological level as follows. As a retrovirus, HIV uses the enzyme reverse transcriptase to synthesize DNA from its RNA genome and lacks a mechanism for correcting errors made while reproducing its genome. As a result, HIV replicates its genome with the highest known mutation rate of any 'living' organism. This creates an ideal situation for natural selection to act on the HIV population, as genetic variation is the raw material for natural selection.

These mutations accumulate over generations and in populations, resulting in the great genetic variation within populations of HIV, and an increased probability of a virion developing an evolutionary selective advantage over other virions. Natural selection then acts on HIV by selecting for virions with higher fitness, as all others are eventually killed off by drug treatments. The virions that are able to escape the harmful effects of the drug then create an entirely new, drug resistant population.

The consequence of a decline in a prior treatment effectiveness is that the virions reproduce until the patient has an increased, detectable population of viruses, for example as large as before treatment. This creates a cycle in which patients, especially HIV-positive patients, first experience success with treatment, as:

their viral load is controlled or even decreased;
their level of CD4+ cell count is maintained or even restored; and/or
the clinical signs which are generally associated with a virus-related condition such as AIDS are stabilized or even disappear. The clinical signs of AIDS vary, depending on the phase of infection.

Then, over time, those patients may experience a decline in treatment effectiveness as the virus develops resistance and rebuilds its population of virus particles.

In particular, this phenomenon is enhanced for anti-HIV therapies, at least for three reasons which include:

(i) the fact that HIV is a retrovirus, and the appearance of novel mutant strains is particularly important for this class of viruses, as stated previously;

(ii) the fact that HIV has the ability to enter into a latent phase and thus form "latent" reservoirs which are not efficiently targeted by the currently available treatments;

(iii) the fact that current available treatments also tend to select HIV mutant strains over time, which in the long-term has a major role in the emergence of drug resistance.

Therefore, there remains a need for compounds which deliver a long lasting reduction of the viral load after treatment termination.

There also remains a need for compounds which produce a long-lasting therapeutic effect on the viral load after treatment termination.

There still exist needs to provide compounds that may be administered over a shorter period, or at longer intervals, than standard treatments, providing the potential to reduce healthcare costs and offer a broader access to treatment.

In particular, there is a continuing need for new drugs, in particular those acting through new and as yet unexplored mechanisms of action to achieve infection control or cure for patients for which a decline in a prior treatment effectiveness has been stated, and also due to the formation of mutants that are resistant to treatment.

Thus, there also remains a need to find and optimize therapeutic approaches to treat or prevent patients infected by viruses, in particular HIV-positive patients demonstrating resistance to classical treatments.

Recently some quinoline derivatives have been described in the following patent applications: WO2010/143169, WO2012080953, EP14306164, and EP14306166 useful in the treatment of AIDS or of inflammatory diseases.

SUMMARY OF THE INVENTION

The invention relates to a quinoline derivative of formula (I) as defined herein after, or anyone of its pharmaceutically acceptable salts and metabolites, for use for treating or preventing a viral infection, in particular a HIV infection or a HIV-related condition in a patient; and then terminating said treatment when: the viral load is low or undetectable; and/or the level of CD4+ cell count is maintained or restored.

The invention also relates to a quinoline derivative of formula (I) as defined herein after, or anyone of its pharmaceutically acceptable salts and metabolites, for use for treating or preventing a viral infection, in particular a HIV infection or a HIV-related condition in a patient, for which an ineffectiveness in prior anti-retroviral treatment, or a decline in prior anti-retroviral treatment effectiveness has been stated.

The invention also relates to a quinoline derivative of formula (I) as defined herein after, or anyone of its pharmaceutically acceptable salts and metabolites, for use for treating or preventing a viral infection, in particular a HIV infection or a HIV-related condition in a patient, wherein the patient is infected by a drug-resistant viral strain, and particularly by a drug-resistant HIV strain.

BRIEF DESCRIPTION OF THE FIGURES

FIG. 1. Potency of quinoline derivatives to inhibit HIV-1 production in PBMC- and macrophages-infected cells. A) HIV-1 strain Ada-MR5 was used to infect triplicate of activated PBMCs from different donors (stimulated for two days with PHA and IL2) in the absence or presence of increasing concentrations of Compound 22, as defined hereafter and more particularly in table A. Supernatant was harvested 6 days post-infection (pi) and viral capsid protein p24 antigen was quantitated using standard ELISA protocol. Each point represents 6 donors. B) HIV-1 strain YU2 was used to infect triplicate of monocyte derived-macrophages from different donors in the absence or presence of increasing concentrations of Compound 22. Supernatant was harvested 8 days pi and viral capsid protein p24 antigen was quantitated using standard ELISA protocol. Each point represents 8 donors.

FIG. 2. HIV p24 inhibition of Compound 22 from different HIV-1 strains. A) Different HIV-1 strains (clade B, clade C and recombinants clades) were used to infect PBMCs from three different donors in the absence of presence of 5 µM of Compound 22. Supernatant was harvested 6 days pi and viral capsid protein p24 antigen was quantitated using standard ELISA protocol. B) RT activity (cpm) measured in human PBMCs infected with different resistant mutants of NL4.3 strain (K103N, K65R and M184V) and treated with Compound 22 or 3TC.

DETAILED DESCRIPTION OF THE INVENTION

Figure 3C:
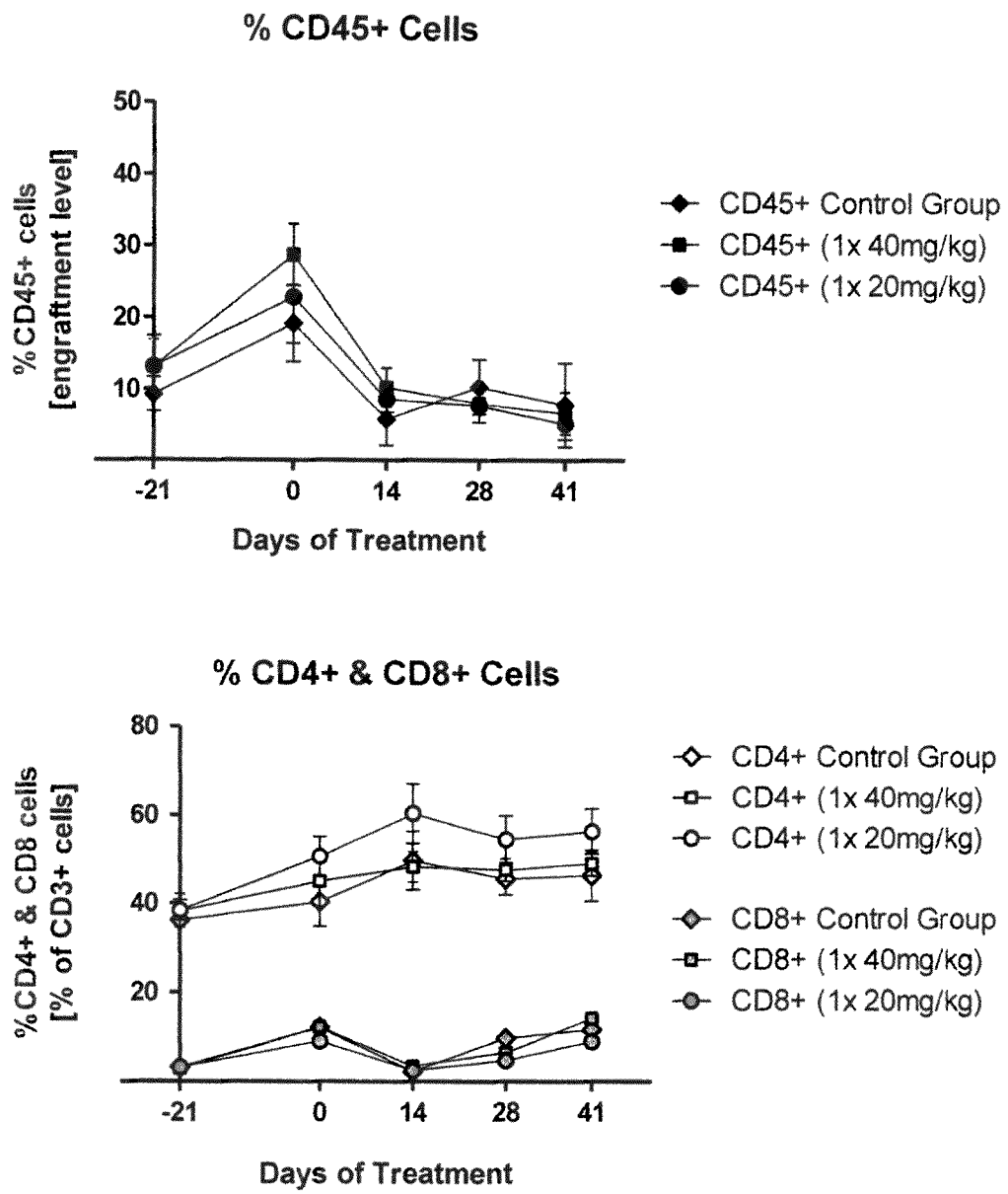
FIG. 3. Efficacy of Compound 22 to inhibit viral replication in humanized mice. A) Reconstituted SCID mice were infected with JRCSF HIV-1 strain by intraperitoneal injection. Control group received by gavage labrafil and 5% DMSO (n=15) and treated group 20 mg/kg b.i.d of Compound 22 in labrafil and 5% DMSO (n=14) for 15 days. Two independent experiments were performed with 5 and 10 reconstituted mice for each group. Viral load was assessed by measuring viral RNA using the Amplicor HIV-1 Monitor from Roche. B) FACS analysis was performed on peritoneal wash at day 15 post-treatment to assess the CD8/CD4 ratio. C) Engrafted NSG humanized mice were treated by oral gavage with Compound 22 at either 20 mg or 40 mg/kg once a day for 30 days and indicated lymphocyte populations (CD45+; CD4+ and CD8+) were monitored by FACS analysis. D) NSG humanized mice were infected with the YU2 HIV-1 virus and treated either by oral gavage with Compound 22 at 40 mg/kg once a day for 30 days or by HAART (3TC-Tenofovir-Raltegravir and AZT). For HAART, food pellets were made by mixing 2.5 g of 3TC, TDF and AZT each, and 5 g of RTV with 5 kg of ground protein-rich, vitamin-fortified food (Nafag 3432, Provimi Kliba AG, Switzerland) which was subsequently formed to food pellets and sterilized by gamma-irradiation with 25 kGy. Viral load was assessed by measuring viral RNA using the Amplicor HIV-1 Monitor from Roche.

The present invention has for purpose to meet the aforementioned needs.

It is shown in the examples herein that quinoline derivatives of the invention reduce HIV replication in HIVs-infected mammals.

More specifically, it is shown herein that such quinoline derivatives (i) reduce HIV-1 viral load in HIV-infected mammals, (ii) maintain or restore a high level of CD4+ cell count in HIV-infected mammals.

The inventors further provide evidence that those quinoline derivatives have long-term treatment effect in patients, and are suitable for treating or preventing a viral infection or a virus-related condition.

As used herein, "patient" may extend to humans or mammals, such as cats or dogs. As used herein, <<preventing>> also encompasses <<reducing the likelihood of occurrence>> or <<reducing the likelihood of reoccurrence>>.

Without wishing to be bound by any particular theory, the inventors are of the opinion that such quinoline derivatives have unexpected properties in targeting latent virus reservoirs, in particular latent HIV reservoirs.

Also, the above-mentioned compounds have a large spectrum of action, but are not prone to confer the development of resistant strains, and do not lead to adverse effects.

Crucially, there was no or reduced or delayed rebound of viral load for at least two months following treatment cessation whereas viral load increased dramatically just one week after stopping ART treatment. Otherwise said, the inventors provide evidence that the quinoline derivatives of the invention, when administered to an HIV-infected patient, are able to maintain a low viral load, even after treatment termination. Thus, the above-mentioned compounds may also be less frequently administered and/or over a shorter period than standard treatments.

The above-mentioned compounds are particularly suitable for treating or preventing a viral infection or a virus-related condition in treatment-resistant individuals, especially individuals infected with a resistant HIV-strain, including HAART-resistant and ART-resistant individuals.

In particular, the above-mentioned methods are particularly suitable for treating or preventing a viral infection or a virus-related condition, for example in Lamivudin (3TC)-resistant, Tenofovir-resistant, Raltegravir-resistant and Azidothymidine (AZT)-resistant individuals.

As used herein, an "anti-retroviral agent" or "anti-retroviral treatment", or more specifically an "anti-HIV agent" or "anti-HIV treatment" means a classical drug, or combination of drugs, administered to fight the viral infection, especially the HIV infection. It may in particular be ART (Antiretroviral Therapy) or HAART (Highly Active Antiretroviral Therapy).

ART and HAART are known in the Art and generally relate to combinations of two, three or more antiretroviral medicines. Such antiretroviral medicines encompass:

(i) nucleoside/nucleotide reverse transcriptase inhibitors also called nucleoside analogs, such as abacavir, emtricitabine, and tenofovir;

(ii) non-nucleoside reverse transcriptase inhibitors (NNRTIs), such as efavirenz, etravirine, and nevirapine;

(iii) protease inhibitors (PIs), such as atazanavir, darunavir, and ritonavir;

(iv) entry inhibitors, such as enfuvirtide and maraviroc;

(v) integrase inhibitors, such as dolutegravir and raltegravir.

Other examples of anti-retroviral agents include, in a non-limitative manner: Zidovudine, Lamivudine, Emtricitabine, Didanosine, Stavudine, Abacavir, Zalcitabine, Tenofivir, Racivir, Amdoxovir, Apricitabine, Elvucitabine, Efavirenz, Nevirapine, Etravirine, Delavirdine, Rilpvirine, Tenofovir, Fosalvudine, Amprenavir, Tipranavir, Indinavir, Saquinavir, Fosamprenavir, Ritonavir, Darunavir, Atazanavir, Nelfinavir, Lopinavir, Raltegravir, Elvitegravir, Dolutegravir, Enfuvirtide, Maraviroc, Vicriviroc, and combinations thereof.

As used herein, an "anti-HIV treatment" or "anti-retroviral treatment" encompasses in particular:

the action of an anti HIV-agent in reducing the viral load during a determined period, but not necessarily showing a long-lasting lowering of said viral load after termination of said treatment;

the action of an anti HIV-agent in increasing the level of CD4+ cell count in HIV-infected patients, but not necessarily showing a long-lasting increase or stabilisation of said cell count after termination of said treatment.

The above-mentioned compounds are particularly suitable for treating or preventing a viral infection or a virus-related condition, especially an HIV-infection or a HIV-related condition.

Also, the above-mentioned compounds are particularly suitable for treating a latent viral infection, especially a HIV infection in a patient.

Also, the above-mentioned compounds are particularly suitable for eradicating a viral infection or a virus-related condition in patient, in particular an HIV-infection or a HIV-related condition, including eradicating HIV and/or for use as a cure for HIV and HIV-related conditions.

Otherwise said, these results have allowed the inventors to target novel categories of viral infections and patients, including HIV-infected patients, which were previously treated poorly with currently available treatments, especially patients infected with drug-resistant strains, and/or which were no longer responsive to such treatments.

The quinoline derivatives of the invention are useful for the treatment or prevention of all viruses and virus-related conditions, and more particularly for the treatment or prevention of retroviruses, latent viruses and related conditions.

In particular, it has been found that in vivo, one of the quinoline derivative of formula (I) as defined hereinafter, was able to reduce significantly the viral load in HIV-infected mice after daily oral gavage but, more importantly, said compound was able to maintain a reduced viral load, compared to control or HAART-treated mice, up to 50 days after treatment termination (See FIG. 4)

These surprising results have allowed the inventors to design doses and regimens suitable to achieve such long-lasting reduced viral load and use in the treatment of virus infected patients, in particular HIV infected patients, including patients for which a decline in a previous antiretroviral treatment has been stated, and corresponding therapeutic methods.

According to a first embodiment, the invention relates to a quinoline derivative of formula (I) as defined herein after, or anyone of its pharmaceutically acceptable salts and metabolites, for use for treating or preventing of a virus infection or virus-related condition in a patient, in particular a HIV infection or a HIV-related condition, wherein: a low or undetectable viral load is maintained; and/or a CD4+ cell count is stable or increased; after treatment termination.

According to said first embodiment, the invention relates to a quinoline derivative of formula (I) as defined herein after, or anyone of its pharmaceutically acceptable salts and metabolites, for use for treating or preventing a virus infection or virus-related condition in a patient, in particular a HIV infection or a HIV-related condition, and then terminating said treatment, wherein: a low or undetectable viral load is maintained; and/or a CD4+ cell count is stable or increased; after treatment termination According to said first embodiment, the invention relates to a quinoline derivative of formula (I) as defined herein after, or anyone of its pharmaceutically acceptable salts and metabolites, for treating or preventing a virus infection or virus-related condition in a patient, in particular a HIV infection or a HIV-related condition, and then terminating said treatment, when: the viral load is low or undetectable; and/or the level of CD4+ cell count is maintained or restored.

Still, according to said first embodiment, the invention relates to a quinoline derivative of formula (I) as defined herein after, or anyone of its pharmaceutically acceptable salts and metabolites, for treating or preventing a virus infection or virus-related condition in a patient, in particular a HIV infection or a HIV-related condition, and then terminating said treatment, when the viral load is undetectable in the blood plasma of said patient.

According to a second embodiment, the invention relates to a quinoline derivative of formula (I) as defined herein after, or anyone of its pharmaceutically acceptable salts and metabolites, for use in the treatment or prevention of a virus infection or virus-related condition in patient, in particular a HIV infection or a HIV-related condition, for which an ineffectiveness in prior anti-retroviral treatment, or a decline in a prior anti-viral, or anti-retroviral, treatment effectiveness has been stated.

According to a third embodiment, the invention relates to a quinoline derivative of formula (I) as defined herein after, or anyone of its pharmaceutically acceptable salts and metabolites, for use in the treatment or prevention of a virus infection or virus-related condition in patient, in particular a HIV infection or a HIV-related condition, wherein the patient is infected by a drug-resistant strain.

Viruses

In a non-limitative manner, examples of viruses which are considered by the invention include enveloped and naked viruses, which includes DNA viruses, RNA viruses and retroviruses, which includes dsDNA viruses, ssDNA viruses, dsRNA viruses, (+)ssRNA viruses, (−)ssRNA viruses, ssRNA-RT viruses and dsDNA-RT viruses, which includes oncoviruses, lentiviruses and spumaviruses.

The oncoviruses are thus termed because they can be associated with cancers and malignant infections. There may be mentioned, for example, leukemogenic viruses (such as the avian leukemia virus (ALV), the murine leukemia virus (MULV), also called Moloney virus, the feline leukemia virus (FELV), human leukemia viruses (HTLV) such as HTLV1 and HTLV2, the simian leukemia virus or STLV, the bovine leukemia virus or BLV, the primate type D oncoviruses, the type B oncoviruses which are inducers of mammary tumors, or oncoviruses which cause a rapid cancer (such as the Rous sarcoma virus or RSV).

The spumaviruses manifest fairly low specificity for a given cell type or a given species, and they are sometimes associated with immunosuppressive phenomena; that is the case, for example, for the simian foamy virus (or SFV).

The lentiviruses, such as HIV, are thus named because they are responsible for slow-progressing pathological conditions which very frequently involve immunosuppressive phenomena, including AIDS.

Viruses, and in particular retroviruses such as HIV, HTLV-I and HTLV-II, are known to rely upon RNA splicing and splicing regulation in order to spread and disseminate within cells and tissues of an infected individual. Other viruses of interest are viruses pathogenic for human, including but not limited to HSV family viruses (including 1, 2, 6), CMV, VZV, HBV, HCV, Hepatitis E virus, Papilloma viruses, RSV, Rhino viruses, influenza viruses, adenoviruses, EBV, Ebola, Nipah viruses, and other arboviruses, Dengue, Chikungunya, West Nile viruses, Rift valley virus, Japanese encephalitis virus, SRAS other coronaviruses, parvovirus, enteroviruses.

Other viruses of interest are viruses pathogenic for animals, including, but not limited to, influenza, FLV, pestivirus, Hantavirus, and lyssavirus.

In particular, viruses and virus-related conditions which are considered include viruses of which viral replication requires RNA splicing, and/or viral RNA export from the nucleus to the cytoplasm.

Examples of viruses include latent viruses and/or retroviruses and/or viruses which are associated with chronic viral infections.

Viruses which are more particularly considered are RNA viruses and retroviruses, including lentiviruses, and preferably HIV. Accordingly, virus-related conditions which are more particularly considered are associated with a RNA virus or a retrovirus, and preferably HIV.

HIV may include HIV-I, HIV-2 and all subtypes thereof, which includes HIV-I strains belonging to the HIV-I B subtype, HIV-I C subtype, and HIV-I recombinants. Examples include HIV-I strains selected from Ad8, AdaM, Isolate B, Isolate C, CRF01, CRF02 and CRF06.

Typical resistant strains are more particularly described in Pinar Iyodogan et al., ("Current Perspectives on HIV-1 Antiretroviral Drug Resistance", Viruses 2014, 6, 4095-4139; doi10.3390/4095).

Advantageously, viruses may include HIV-strains which have developed resistances for current treatments.

According to a preferred embodiment, the virus-related condition is AIDS.

In a non-limitative manner, examples of viruses which are considered by the invention include enveloped and naked viruses, which includes DNA viruses, RNA viruses and retroviruses, which includes dsDNA viruses, ssDNA viruses, dsRNA viruses, (+)ssRNA viruses, (−)ssRNA viruses, ssRNA-RT viruses and dsDNA-RT viruses, which includes oncoviruses, lentiviruses and spumaviruses.

Examples of viruses include latent viruses and/or retroviruses.

According to preferred and exemplary embodiments, the virus is HIV, which includes HIV-1 and HIV-2, and the virus-related condition is AIDS.

Compound of Formula (I)

The quinoline derivatives are preferably selected from compounds disclosed in the following patent applications: WO2010/143169, WO2012080953, EP14306164, and EP14306166.

Such compounds may be prepared according to the synthetic routes as described in said patent applications.

The quinoline derivative of formula (I) according to the present invention is a compound of formula (I):

$$\text{Rn} - \underset{Z}{\overset{V}{\underset{|}{\bigcirc}}} - \underset{R''}{Q} - \underset{N}{\bigcirc} - R'_{n'} \qquad (I)$$

wherein:
z represents N or C, $$\underset{Z}{\overset{V}{\bigcirc}}$$

means an aromatic ring wherein V is C or N and when V is N, V is in ortho, meta or para of z, i.e. forms respectively a pyridazine, a pyrimidine or a pyrazine group, R independently represent a hydrogen atom, a halogen atom or a group chosen among a —CN group, a hydroxyl group, a —COOR$_1$ group, a $(C_1$-$C_3)$fluoroalkyl group, a $(C_1$-$C_3)$fluoroalkoxy group, a $(C_3$-$C_6)$cycloalkyl group, a —NO$_2$ group, a —NR$_1$R$_2$ group, a $(C_1$-$C_4)$alkoxy group, a phenoxy group, a —NR$_1$—SO$_2$—NR$_1$R$_2$ group, a —NR$_1$—SO$_2$—R$_1$ group, a —NR$_1$—C(=O)—R$_1$ group, a —NR$_1$—C(=O)—NR$_1$R$_2$ group, a —SO$_2$—NR$_1$R$_2$ group, a —SO$_3$H group, a —O—SO$_2$—OR$_3$ group, a —O—P(=O)—(OR$_3$)(OR$_4$) group, a —O—CH$_2$—COOR$_3$ group and a (C$_1$-C$_3$) alkyl group, said alkyl being optionally mono-substituted by a hydroxyl group, Q is N or O, provided that R" does not exist when Q is O, R$_1$ and R$_2$ are independently a hydrogen atom or a (C$_1$-C$_3$)alkyl group, R$_3$ and R$_4$ independently represent a hydrogen atom, Li$^+$, Na$^+$, K$^+$, N$^+$(Ra)$_4$ or a benzyl group, n is 1, 2 or 3, n' is 1, 2 or 3, R' independently represent a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$)alkoxy group and a —CN group, and can further be a group chosen among:

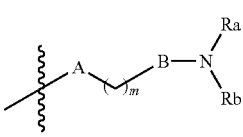
(IIa)

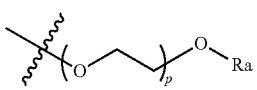
(IIIa)

A is a covalent bond, an oxygen atom or NH,

B is a covalent bond or NH, m is 1, 2, 3, 4 or 5, p is 1, 2 or 3,

Ra and Rb independently represent a hydrogen atom, a (C$_1$-C$_5$)alkyl group or a (C$_3$-C$_6$)cycloalkyl group, Ra and Rb can further form together with the nitrogen atom to which they are attached a saturated 5- or 6-membered heterocycle optionally containing a further heteroatom chosen among N, O and S, said heterocycle being optionally substituted by one or more Ra, provided that when R' is a group (IIa) or (IIIa), n' may be 2 or 3 only if other R' groups are different from said group (IIa) or (IIIa), R" is a hydrogen atom, a (C$_1$-C$_4$)alkyl group or is a group (IIa) as defined above, or anyone of its pharmaceutically acceptable salt.

The present invention is also directed to the implementation of the active metabolites of the herein above defined compounds of formula (I), more particularly human metabolites, for example N-glucuronide metabolites thereof. In particular, the use of the N-glucuronide of compound 22 or one of its pharmaceutically acceptable salts, is also encompassed within the framework of the claimed subject-matter. Said N-glucuronide metabolite has the following formula

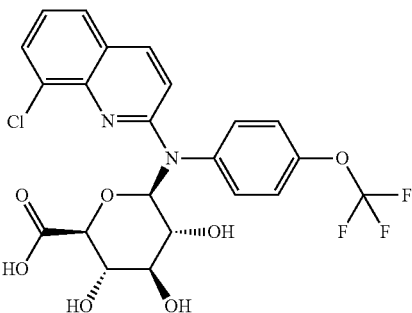 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

It is shown herein that those metabolites demonstrate an anti-viral activity and more particularly an anti-HIV activity. They can be administered and themselves administered as active ingredients. The N-glucuronide as more particularly described above may be prepared according to the synthetic route as described in patent application EP15305274.

According to a preferred embodiment, Q is N.

According to another preferred embodiment, n is 1 or 2.

According to another preferred embodiment, n' is 1 or 2.

According to another preferred embodiment, R" is a hydrogen atom, a (C$_1$-C$_4$)alkyl group or a group

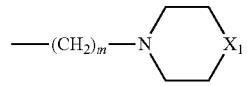

wherein m is 2 or 3 and X$_1$ is O, CH$_2$ or N—CH$_3$.

According to another preferred embodiment, R independently represent a hydrogen atom, a methyl group, a methoxy group, a trifluoromethyl group, a halogen atom and more particularly a fluorine or chlorine atom, a trifluoromethoxy group and an amino group.

According to another preferred embodiment, R' independently represent a hydrogen atom, a halogen atom and more particularly a fluorine or chlorine atom, an amino group, a methyl group or a group

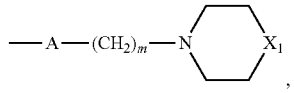

wherein A is O or NH, m is 2 or 3 and X$_1$ is O, CH$_2$ or N—CH$_3$, provided that when R' is such a group, n' is 1 or 2, and when n' is 2, the other R' group is different from said group.

According to one aspect of said preferred embodiment, R' alternatively independently represent a hydrogen atom, a halogen atom and more particularly a fluorine or chlorine atom, a methyl group or a group

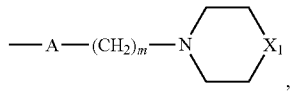

wherein A is O or NH, m is 2 and X$_1$ is O, CH$_2$ or N—CH$_3$, provided that when R' is such a group, n' is 1 or 2, and when n' is 2, the other R' group is different from said group.

All the prior and following particular embodiments may of course be combined together and form part of the invention.

Compounds of formula (I) include compounds of formula (Ia), (Ib), (Ic), (Id) and (Ie), as defined herebelow.

According to a Particular Embodiment, a Quinoline Derivative of Formula (I) May be a Compound of Formula (Ia)

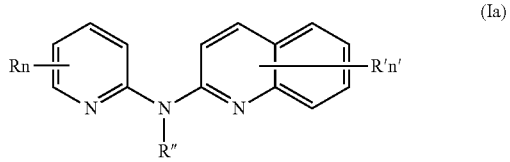

(Ia)

wherein R, R', R", n and n' are as defined above.

According to one aspect of said preferred embodiment, n is 1 or 2.

According to one aspect of said preferred embodiment, n' is 1 or 2.

According to one aspect of said preferred embodiment, R independently represent a hydrogen atom, a halogen atom or a group chosen among a hydroxyl group, a $(C_1-C_3)$fluoroalkyl group, a $(C_1-C_3)$ fluoroalkoxy group, a $—NR_1R_2$ group, a $(C_1-C_4)$alkoxy group and a $(C_1-C_3)$alkyl group.

According to one aspect of said preferred embodiment, R' independently represent a hydrogen atom, a halogen atom or a group chosen among a $(C_1-C_3)$alkyl group, a hydroxyl group, a $—NR_1R_2$ group, or a group

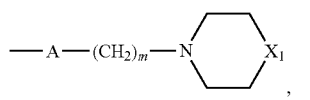

wherein A is O or NH, m is 2 or 3 and $X_1$ is O, $CH_2$ or N—$CH_3$, provided that when R' is such a group, n' is 1 or 2 and when n' is 2, the other R' group is different from said group.

According to one aspect of said preferred embodiment, R" is a hydrogen atom, a $(C_1-C_4)$alkyl group or a group

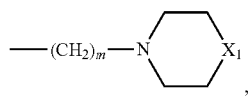

wherein m is 2 or 3 and $X_1$ is O, $CH_2$ or N—$CH_3$, and preferably R" is a hydrogen atom or a methyl group.

According to a Particular Embodiment, a Quinoline Derivative of Formula (I) May be a Compound of Formula (Ib)

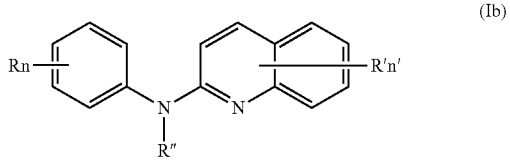

(Ib)

wherein R, R', R", n and n' are as defined above.

According to one aspect of said preferred embodiment, n is 1 or 2.

According to one aspect of said preferred embodiment, n' is 1, 2 or 3.

According to one aspect of said preferred embodiment, R independently represent a hydrogen atom, a halogen atom or a group chosen among a hydroxyl group, a $(C_1-C_3)$fluoroalkyl group, a $(C_1-C_3)$fluoroalkoxy group, a $—NR_1R_2$ group, a $(C_1-C_4)$alkoxy group and a $(C_1-C_3)$alkyl group.

According to one aspect of said preferred embodiment, R' independently represent a hydrogen atom, a halogen atom or a group chosen among a $(C_1-C_3)$alkyl group, a hydroxyl group, a $—NR_1R_2$ group, or a group

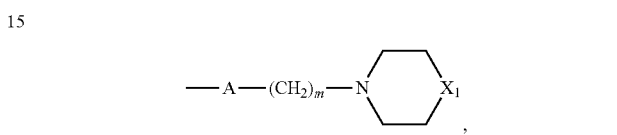

wherein A is O or NH, m is 2 or 3 and $X_1$ is O, $CH_2$ or N—$CH_3$, provided that when R' is such a group, n' is 1 or 2, and when n' is 2, with the other R' group is different from said group.

According to one aspect of said preferred embodiment, R' alternatively independently represent a hydrogen atom, a halogen atom or a group chosen among a $(C_1-C_3)$alkyl group, a hydroxyl group or a $—NR_1R_2$ group.

According to one aspect of said preferred embodiment, R" is a hydrogen atom, a $(C_1-C_4)$alkyl group or a group

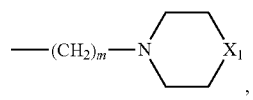

wherein m is 2 or 3 and $X_1$ is O, $CH_2$ or N—$CH_3$, and preferably R" is a hydrogen atom or a methyl group.

According to a Particular Embodiment, a Quinoline Derivative of Formula (I) May be a Compound of Formula (Ic)

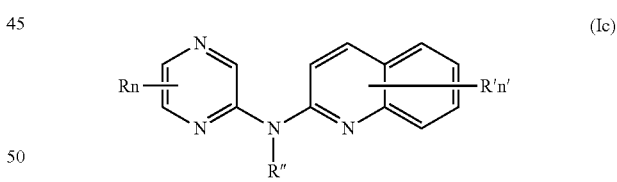

(Ic)

wherein R, R', R", n and n' are as defined above.

According to one aspect of said preferred embodiment, n is 1.

According to one aspect of said preferred embodiment, n' is 1.

According to one aspect of said preferred embodiment, R independently represent a hydrogen atom, a halogen atom or a group chosen among a hydroxyl group, a $(C_1-C_3)$ fluoroalkyl group, a $(C_1-C_3)$ fluoroalkoxy group, a $—NR_1R_2$ group, a $(C_1-C_4)$ alkoxy group and a $(C_1-C_3)$ alkyl group.

According to one aspect of said preferred embodiment, R alternatively independently represent a hydrogen atom or a halogen atom.

According to one aspect of said preferred embodiment, R' independently represent a hydrogen atom, a halogen atom or a group chosen among a $(C_1\text{-}C_3)$ alkyl group, a hydroxyl group, a —$NR_1R_2$ group, or a group

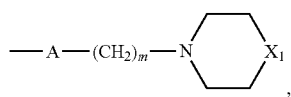

wherein A is O or NH, m is 2 or 3 and $X_1$ is O, $CH_2$ or N—$CH_3$, provided that when R' is such a group, n' is 1 or 2 and when n' is 2, the other R' group is different from said group.

According to one aspect of said preferred embodiment, R' alternatively independently represent a hydrogen atom or a halogen atom.

According to one aspect of said preferred embodiment, R" is a hydrogen atom, a $(C_1\text{-}C_4)$alkyl group or a group

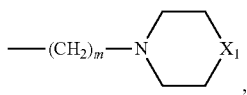

wherein m is 2 or 3 and $X_1$ is O, $CH_2$ or N—$CH_3$, and preferably R" is a hydrogen atom or a methyl group.

According to a Particular Embodiment, a Quinoline Derivative of Formula (I) May be a Compound of Formula (Id)

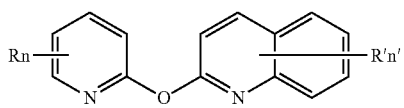

wherein R, R', n and n' are as defined above.

According to one aspect of said preferred embodiment, n is 1.

According to one aspect of said preferred embodiment, n' is 1.

According to one aspect of said preferred embodiment, R independently represent a hydrogen atom, a halogen atom or a group chosen among a hydroxyl group, a $(C_1\text{-}C_3)$fluoroalkyl group, a $(C_1\text{-}C_3)$fluoroalkoxy group, a —$NR_1R_2$ group, a $(C_1\text{-}C_4)$alkoxy group and a $(C_1\text{-}C_3)$alkyl group.

According to one aspect of said preferred embodiment, R alternatively independently represent a hydrogen atom, a $(C_1\text{-}C_3)$fluoroalkyl group, a $(C_1\text{-}C_3)$fluoroalkoxy group or a halogen atom.

According to one aspect of said preferred embodiment, R' independently represent a hydrogen atom, a halogen atom or a group chosen among a $(C_1\text{-}C_3)$alkyl group, a hydroxyl group, a —$NR_1R_2$ group, or a group

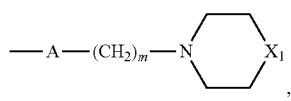

wherein A is O or NH, m is 2 or 3 and $X_1$ is O, $CH_2$ or N—$CH_3$, provided that when R' is such a group, n' is 1 or 2 and when n' is 2, the other R' group is different from said group.

According to one aspect of said preferred embodiment, R' alternatively independently represents a hydrogen atom or a halogen atom.

According to one aspect of said preferred embodiment, R" is a hydrogen atom, a $(C_1\text{-}C_4)$alkyl group or a group

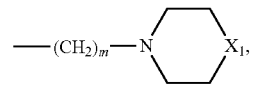

wherein m is 2 or 3 and $X_1$ is O, $CH_2$ or N—$CH_3$, and preferably R" is a hydrogen atom or a methyl group.

According to a Particular Embodiment, a Quinoline Derivative of Formula (I) May be a Compound of Formula (Ie)

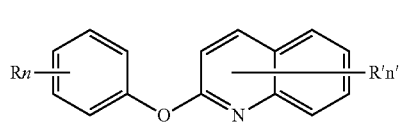

wherein R, R', n and n' are as defined above.

According to one aspect of said preferred embodiment, n is 1.

According to one aspect of said preferred embodiment, n' is 1.

According to one aspect of said preferred embodiment, R independently represent a hydrogen atom, a halogen atom or a group chosen among a hydroxyl group, a $(C_1\text{-}C_3)$fluoroalkyl group, a $(C_1\text{-}C_3)$fluoroalkoxy group, a —$NR_1R_2$ group, a $(C_1\text{-}C_4)$alkoxy group and a $(C_1\text{-}C_3)$alkyl group.

According to one aspect of said preferred embodiment, R alternatively independently represent a hydrogen atom, a $(C_1\text{-}C_3)$fluoroalkyl group, a $(C_1\text{-}C_3)$fluoroalkoxy group or a halogen atom.

According to one aspect of said preferred embodiment, R' independently represent a hydrogen atom, a halogen atom or a group chosen among a $(C_1\text{-}C_3)$alkyl group, a hydroxyl group, a —$NR_1R_2$ group, or a group

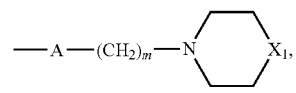

wherein A is O or NH, m is 2 or 3 and $X_1$ is O, $CH_2$ or N—$CH_3$, provided that when R' is such a group, n' is 1 or 2 and when n' is 2, the other R' group is different from said group.

According to one aspect of said preferred embodiment, R' alternatively independently represent a hydrogen atom or a halogen atom.

According to one aspect of said preferred embodiment, R" is a hydrogen atom, a $(C_1\text{-}C_4)$alkyl group or a group

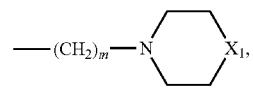

wherein m is 2 or 3 and $X_1$ is O, $CH_2$ or N—$CH_3$, and preferably R" is a hydrogen atom or a methyl group.

According to one exemplary embodiment, the quinoline derivative may be chosen among (with the number to be found in table A hereinafter):
(1) 8-chloro-3-methyl-N-2-(4-(trifluoromethyl)pyridin-2-yl)quinoline-2,5-diamine
(2) 8-chloro-N-2-(4-(trifluoromethyl)pyridin-2-yl)quinoline-2,5-diamine
(3) 8-chloro-5-(2-morpholinoethoxy)-N-(4-(trifluoromethyl)pyridine-2-yl)quinolin-2-amine
(4) 8-chloro-N4-(3-(piperidin-1-yl)propyl)-N-2-(4-(trifluoromethyl)pyridin-2-yl)quino line-2,4-diamine
(5) 8-chloro-6-(2-morpholinoethoxy)-N-(4-(trifluoromethyl)pyridin-2-yl)quinolin-2-amine
(6) 8-chloro-N-methyl-N-(4-(trifluoromethyl)pyridin-2-yl)quinolin-2-amine
(7) 8-chloro-N-(4-(trifluoromethyl)pyridin-2-yl)quinolin-2-amine
(8) 4,8-dichloro-N-(4-(trifluoromethyl)pyridin-2-yl)quinolin-2-amine
(9) 8-chloro-N-(3-morpholinopropyl)-N-(4-(trifluoromethyl)pyridin-2-yl)quinolin-2-amine
(10) 8-chloro-5-(2-(piperidin-1-yl)ethoxy)-N-(4-(trifluoromethyl)pyridin-2-yl)quinolin-2-amine
(11) (8-chloro-quinolin-2-yl)-(4-methyl)pyridin-2-yl)-amine
(12) 8-chloro-N-(5-fluoropyridin-2-yl)quinolin-2-amine
(13) N-(3-methoxypyridin-2-yl)quinolin-2-amine
(14) N-(6-(trifluoromethyl)pyridin-2-yl)quinolin-2-amine
(15) 6-chloro-N-(5-fluoropyridin-2-yl)quinolin-2-amine
(16) N-(3-fluoropyridin-2-yl)quinolin-2-amine
(17) 8-chloro-N-(6-(trifluoromethyl)pyridin-2-yl)quinolin-2-amine
(18) 8-chloro-N-(3-chloro-4-methoxyphenyl)quinolin-2-amine
(19) 8-chloro-N-(4-(methoxy)phenyl)quinolin-2-amine
(20) 3-Methyl-N-(4-(trifluoromethoxy)phenyl)quinolin-2-amine
(21) 8-chloro-N-(3-(piperidin-1-yl)propyl)-N-(4-(trifluoromethoxy)phenyl)quinolin-2-amine
(22) 8-chloro-N-(4-(trifluoromethoxy)phenyl)quinolin-2-amine
(23) 4,8-dichloro-N-(4-(trifluoromethoxy)phenyl)quinolin-2-amine
(24) 8-chloro-N-methyl-N-(4-(trifluoromethoxy)phenyl)quinolin-2-amine
(25) 8-chloro-N-(2-morpholinoethyl)-N-(4-(trifluoromethoxy)phenyl)quinolin-2-amine
(26) 8-chloro-N-(pyrazin-2-yl)quinolin-2-amine
(27) 8-chloro-2-((4-(trifluoromethyl)pyridin-2-yl)oxy)quino line
(28) 4-(2-((8-chloro-2-((4-(trifluoromethyl)pyridin-2-yl)oxy)quinolin-6-yl)oxy)ethyl)morpholine
(29) 8-chloro-2-(4-(trifluoromethoxy)phenoxy)quino line
(30) 4-(2-((8-chloro-2-(4-(trifluoromethoxy)phenoxy)quinolin-5-yl)oxy)ethyl)morpholine For the purpose of the present invention, a quinoline derivative of formula (I) includes any one of compounds of formula (Ia), (Ib), (Ic), (Id) and (Ie), as well as combinations thereof. Compounds of formula (I) include compounds (1) to (30), as defined in Table A, and combinations thereof.

The compounds of the invention may exist in the form of free bases or of addition salts with pharmaceutically acceptable acids.

Suitable physiologically acceptable acid addition salts of compounds of formula (I) include hydrobromide, tartrate, citrate, trifluoroacetate, ascorbate, hydrochloride, tartrate, triflate, maleate, mesylate, formate, acetate and fumarate.

The compounds of formula (I) and or salts thereof may form solvates or hydrates and the invention includes all such solvates and hydrates.

The terms "hydrates" and "solvates" simply mean that the compounds (I) according to the invention can be in the form of a hydrate or solvate, i.e. combined or associated with one or more water or solvent molecules. This is only a chemical characteristic of such compounds, which can be applied for all organic compounds of this type.

The compounds of formula (I) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

In the context of the present invention, the term:

"halogen" is understood to mean chlorine, fluorine, bromine, or iodine, and in particular denotes chlorine, fluorine or bromine, "$(C_1-C_5)$alkyl" as used herein respectively refers to $C_1-C_5$ normal, secondary or tertiary saturated hydrocarbon. Examples are, but are not limited to, methyl, ethyl, 1-propyl, 2-propyl, butyl, pentyl, "$(C_3-C_6)$cycloalkyl" as used herein respectively refers to cyclic saturated hydrocarbon. Examples are, but are not limited to cyclopropyl, cyclobutyl, cyclopentyl, cyclohexyl, "$(C_1-C_4)$alkoxy" as used herein respectively refers to O—$(C_1-C_4)$alkyl moiety, wherein alkyl is as defined above. Examples are, but are not limited to, methoxy, ethoxy, 1-propoxy, 2-propoxy, butoxy, "fluoroalkyl group" and "fluoroalkoxy group" refers respectively to alkyl group and alkoxy group as above-defined, said groups being substituted by at least one fluorine atom. Examples are perfluoroalkyl groups, such as trifluoromethyl or perfluoropropyl, "saturated 5- or 6-membered heterocycle" as used herein respectively refers to a saturated cycle comprising at least one heteroatom. Examples are, but are not limited to, morpholine, piperazine, thiomorpholine, piperidine and pyrrolidine.

The chemical structures of some compounds of formula (I) of the invention are illustrated in Table A.

TABLE A

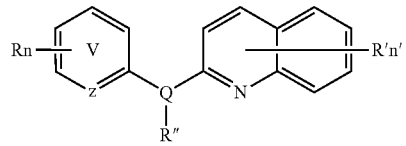

Formula (Ia)

| 1 | 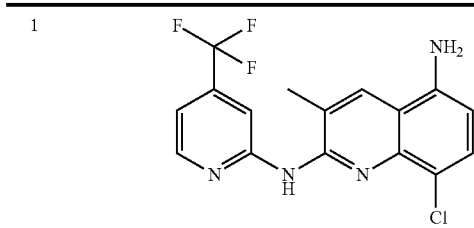 |
|---|---|

TABLE A-continued
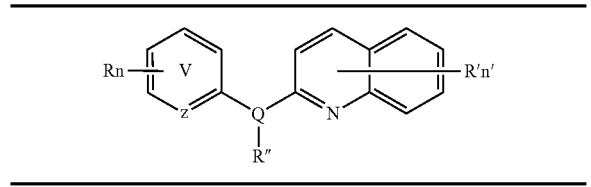
| 2 | 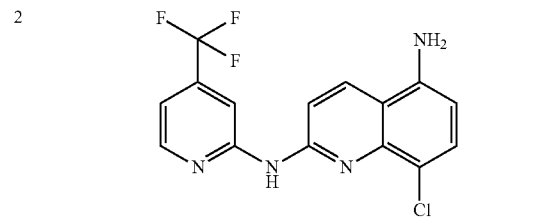 |
| --- | --- |
| 3 | 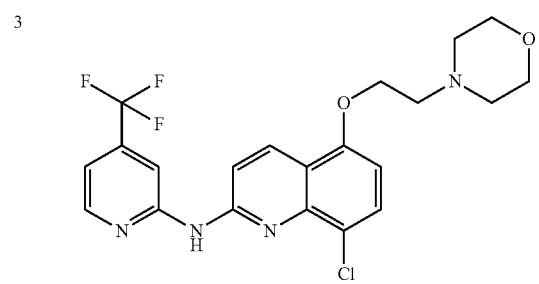 |
| 4 | 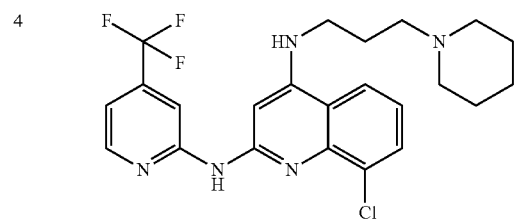 |
| 5 | 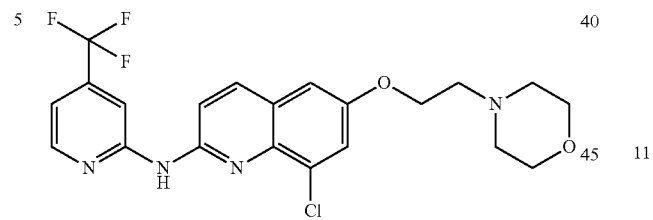 |
| 6 | 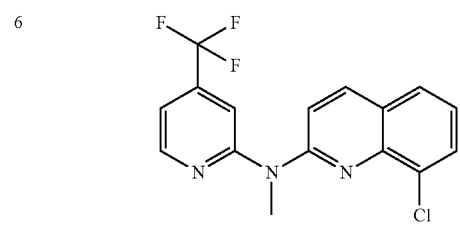 |
| 7 | 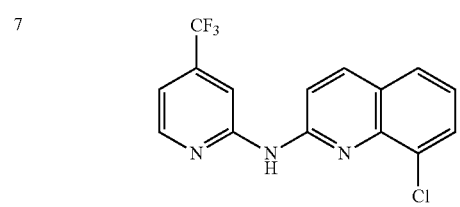 |
| 8 | 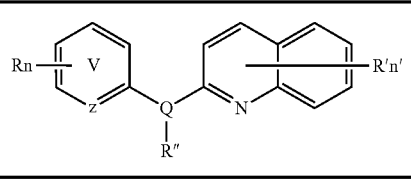 |
| 9 | 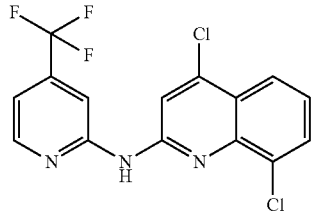 [SMILES: FC(F)(F)c1ccnc(Nc2cc(Cl)c3cccc(Cl)c3n2)c1] |
| 10 | 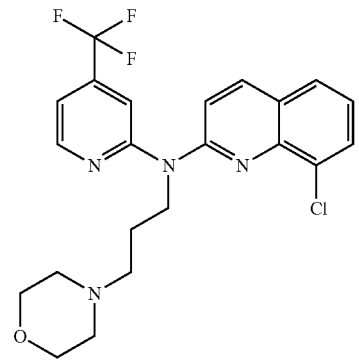 [SMILES: FC(F)(F)c1ccnc(N(CCCN2CCOCC2)c2ccc3cccc(Cl)c3n2)c1] |
| 11 | 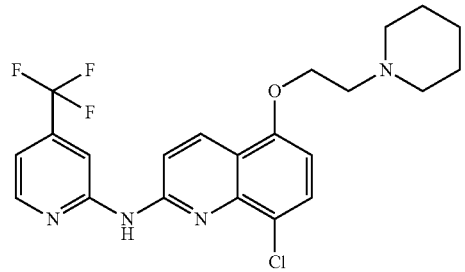 [SMILES: FC(F)(F)c1ccnc(Nc2ccc3c(OCCN4CCCCC4)ccc(Cl)c3n2)c1] |
| 12 | 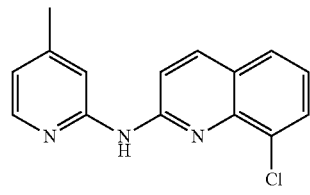 [SMILES: Cc1ccnc(Nc2ccc3cccc(Cl)c3n2)c1] |
| 13 | 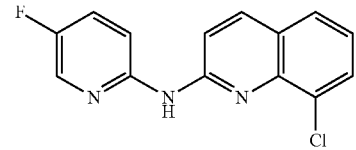 [SMILES: Fc1ccc(Nc2ccc3cccc(Cl)c3n2)nc1] |

TABLE A-continued
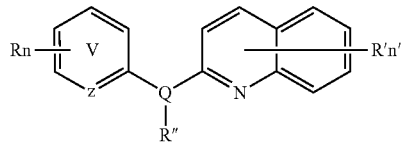
| 14 | 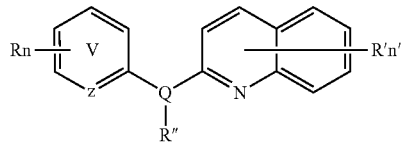 |
| 15 | 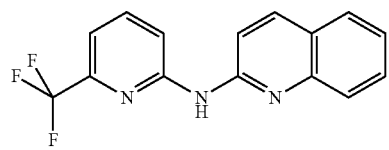 [SMILES: FC(F)(F)c1cccc(Nc2ccc3ccccc3n2)n1] |
| 16 | 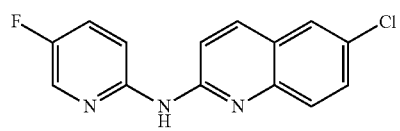 [SMILES: Fc1ccc(Nc2ccc3cc(Cl)ccc3n2)nc1] |
| 17 |  |
Formula (Ib)
| 18 | 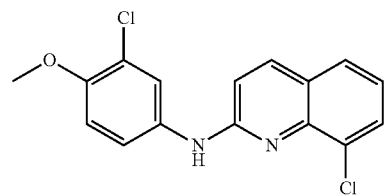 [SMILES: COc1ccc(Nc2ccc3cccc(Cl)c3n2)cc1Cl] |
| 19 | 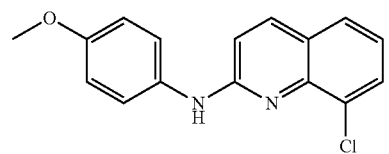 [SMILES: COc1ccc(Nc2ccc3cccc(Cl)c3n2)cc1] |
| 20 | 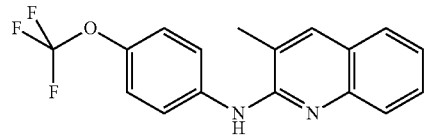 [SMILES: Cc1cc2ccccc2nc1Nc1ccc(OC(F)(F)F)cc1] |
TABLE A-continued
| 21 | 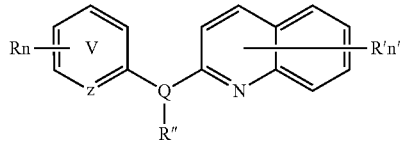 |
| 22 | 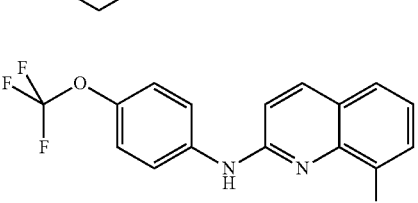 |
| 23 | 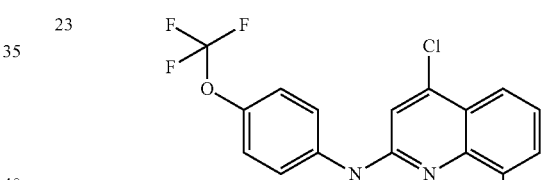 |
| 24 | 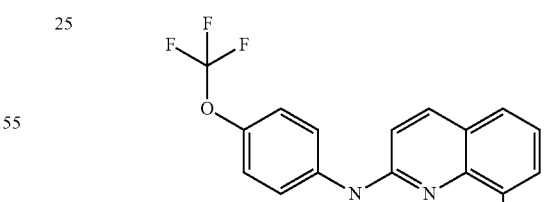 |
| 25 | 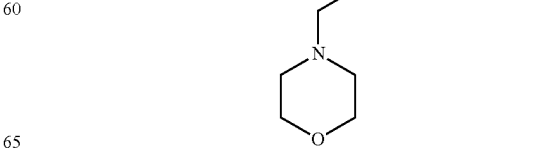 |

TABLE A-continued

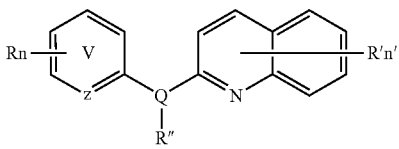

Formula (Ic)

| 26 | 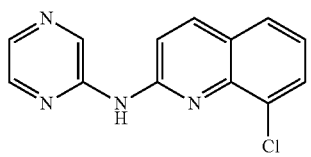 [SMILES: Clc1cccc2ccc(Nc3cnccn3)nc12] |

Formula (Id)

| 27 | 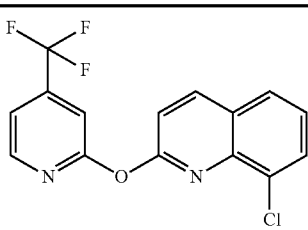 |
| 28 | 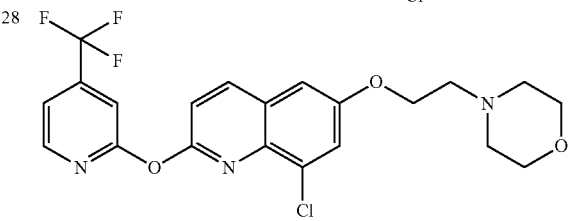 |

Formula (Ie)

| 29 | 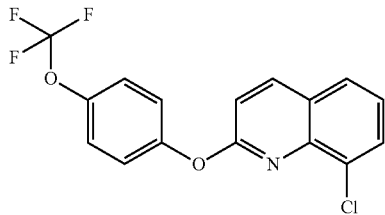 [SMILES: FC(F)(F)Oc1ccc(Oc2ccc3cccc(Cl)c3n2)cc1] |
| 30 | 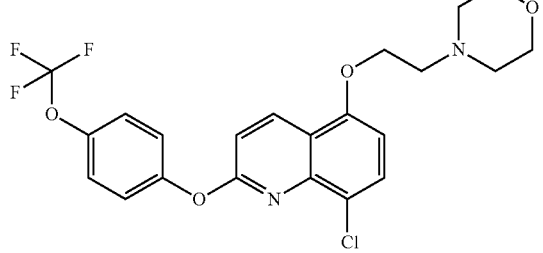 |

Treatment of Drug-Resistant Patients and/or Patients Infected with Resistant Strains According to one aspect of the invention, the present invention concerns a quinoline derivative of formula (I) as described above, for use in the treatment or prevention of a viral infection or a virus-related condition in a patient, in particular infected by HIV, for which a decline in a prior treatment effectiveness has been stated.

As used herein a "prior or preceding treatment" means an anti-HIV treatment that the patient has followed during any time.

The consequences of an ineffectiveness or decline in a prior treatment effectiveness of a HIV infection or HIV-related condition in a patient generally consist of:
 an increase of the HIV viral load; and/or
 a decrease of the level of CD4+ cell count;
 an increase or an appearance of clinical signs which are generally associated with AIDS.

As used herein "a decline in prior treatment effectiveness has been stated" may be indicative that resistant strains of the virus appear during said prior treatment, such strains not being fought by the anti-HIV agent.

In a non-limitative manner, a decline of a prior treatment effectiveness in a patient may occur for instance because:
 the patient is infected with a virus strain, in a particular an HIV strain, of which the replication and/or infectivity was thought to be stabilized or even decreased, but that is not responsive anymore to the treatment, which includes ART and HAART treatment; and/or
 the patient is infected with a drug-resistant strain.

In particular, the definition encompasses previously treated patients, of which the HIV viral load and/or the level of CD4+ cell count remained stable and/or low establishing thereby a reference value, and which upon treatment or after present at least one of the following:
 an increase of the HIV viral load; and/or
 a decrease of the level of CD4+ cell count;
 wherein the HIV viral load and/or the level of CD4+ cell count is/are established preferably in a plasma sample.

In such cases, the statement of the ineffectiveness or decline of the effectiveness of said prior treatment may be assessed by measuring the viral load which has increased above the detectable level, in particular for several consecutive weeks, for example for at least one or two weeks, in particular at least 3 weeks or 4 weeks of treatment with an anti-HIV agent, the viral load being as defined herein after.

Alternatively, the statement of the ineffectiveness or decline of the effectiveness of said prior treatment may be assessed by measurement of CD4+ cell count in blood plasma which has decreased again below 500/mm$^3$, in particular for several consecutive weeks, for example for at least one or two weeks, in particular at least 3 weeks or 4 weeks of treatment with an anti-HIV agent, the CD4+ cell count being defined in more details herein after.

Accordingly, the statement of the ineffectiveness or decline of the effectiveness of said prior treatment may be assessed by determining a decrease of the CD4+ cell count below a physiological CD4+ cell count.

For reference, a restored CD4+ cell count may correspond to a physiological (or "normal") CD4+ cell count, which is generally equal or superior to 500 CD4+ cells/mm$^3$ of plasma, which generally varies between 500 and 1500 CD4+ cells/mm$^3$ of plasma, though it may be lower for some individuals.

Alternatively a restored CD4+ cell count may correspond to an increase of the CD4+ cell count, compared to the CD4+ cell count in said patient prior to said treatment.

Accordingly, a low CD4+ cell count includes a CD4+ cell count inferior to 500/mm$^3$ in blood plasma, which includes inferior to 450; 350; 300; 250; 200; 150 and 100/mm$^3$ in blood plasma.

According to one embodiment, the patient is infected with a drug-resistant strain.

The occurrence of a drug-resistant strain in a patient may be a consequence of either:

selection of a drug-resistant strain from said patient after a prior treatment, as disclosed above; and/or primo-infection of the patient with a drug-resistant strain.

Because of the broad efficiency of the quinoline derivatives of the invention, it is now possible to provide novel treatment strategies, even for primo-infected patients with otherwise untreatable strains.

As used herein, "HIV drug resistance" relates to the ability of HIV to mutate and reproduce itself in the presence of antiretroviral drugs.

For reference, a "drug-resistant HIV strain" may be determined by measuring the Reverse Transcriptase (RT) activity in human PBMCs infected with the tested strain, and then treated with the compound or combination of compound for which a resistance is suspected, as defined in Example 1 and FIG. 2.

Accordingly, the patient has not necessarily been treated previously by an anti-viral treatment, including anti-retroviral treatment or even an anti-HIV-treatment different from said quinoline derivative.

Accordingly, the invention further relates to a quinoline derivative of formula (I) as defined above, or anyone of its metabolites, for use in the treatment or prevention of a HIV infection or a HIV-related condition in a patient, wherein: a low or undetectable viral load is maintained; and/or a CD4+ cell count is stable or increased; after treatment termination and for which the patient has not been treated previously by an anti-retroviral treatment.

Accordingly, the invention further relates to a quinoline derivative of formula (I) as defined above, or anyone of its metabolites, for use in the treatment or prevention of a HIV infection or a HIV-related condition in a patient, wherein the patient is infected by a drug-resistant viral strain, and particularly by a drug-resistance HIV strain and for which the patient has not been treated previously by an anti-retroviral treatment.

Examples of drug-resistant HIV strains are selected from: mutants of the NL4.3 strain, including K103N (resistant to Effavirenz), K65R (resistant to Tenofovir and 3TC) and M184V (resistant to 3TC) mutants, HIV-1 B strains and selected from Ad8 and AdaM; and clinical isolates selected from CRF01, CRF02, and CRF06.

In particular, the virus strain may be a strain resistant to a drug or a treatment comprising the administration of a drug selected from ART and/or HAART treatments, and/or (i) nucleoside/nucleotide reverse transcriptase inhibitors also called nucleoside analogs, such as Abacavir, Emtricitabine, and Tenofovir;

(ii) non-nucleoside reverse transcriptase inhibitors (NNRTIs), such as Efavirenz, Etravirine, and Nevirapine;

(iii) protease inhibitors (PIs), such as Atazanavir, Darunavir, and Ritonavir;

(iv) entry inhibitors, such as Enfuvirtide and Maraviroc;

(v) integrase inhibitors, such as Dolutegravir and Raltegravir;

and combinations thereof.

Accordingly, a drug-resistant HIV strain encompasses NRTIs, NNRTIs, PIs, entry inhibitors and integrase inhibitors-resistant HIV strains.

Resistant strains are known in the Art and include, in a non-limitative manner, strains bearing a resistance mutation as disclosed in the International Antiviral Society-USA (IAS-USA) and Stanford HIV drug databases.

Typical resistant HIV strains include strains bearing a resistance mutation selected from:

M41; K65; D67; K70; L74; Y115; M184 (including M184 V/I); L210; T215; K219; as major NRTI resistance mutations;

M41; A62; D67; T69; K70; V75; F77; F116; Q151; L210; T215; K219; as multi-NTRI resistance mutations;

V90; A98; L100; K101; K103; V106; V108; E138; V179; Y181; Y188; G190; H221; P225; F227; M230; as major NNRTI resistance mutations;

L10; V11; G16; K20; L24; D30; V32; L33; E34; M36; K43; M46; I47; G48; I50; F53; I54; Q58; D60; I62; L63; I64; H69; A71; G73; L74; L76; V77; V82; N83; I84; I85; N88; L89; L90; I93 as major Protease Inhibitor resistance mutations;

T66; L74; E92; T97; E138; G140; Y143; S147; Q148; N155 as major Integrase Inhibitor resistance mutations;

G36; I37; V38; Q39; Q40; N42; N43 as major Entry Inhibitor resistance mutations; and combinations thereof.

Of note, particular sub-categories of mutant/resistant strains, including point mutations such as substitutions of one nucleotide with another, are known in the Art and are also considered by the invention.

Examples of drugs for which drug-resistant HIV strains have been found include: Zidovudine, Lamivudine, Emtricitabine, Didanosine, Stavudine, Abacavir, Zalcitabine, Tenofivir, Racivir, Amdoxovir, Apricitabine, Elvucitabine, Efavirenz, Nevirapine, Etravirine, Delavirdine, Rilpvirine, Tenofovir, Fosalvudine, Amprenavir, Tipranavir, Indinavir, Saquinavir, Fosamprenavir, Ritonavir, Darunavir, Atazanavir, Nelfinavir, Lopinavir, Raltegravir, Elvitegravir, Dolutegravir, Enfuvirtide, Maraviroc, Vicriviroc, and combinations thereof.

In particular, the HIV strain that is treated may be resistant to lamivudine (3TC), Tenofovir, Raltegravir, Zidovudine (AZT), Nevirapine (NVP), Efavirenz (EFV) and combinations thereof.

Uses and methods are both considered, in the sense of the invention.

The invention further relates to uses and methods for treating or preventing a viral infection, in particular HIV infection or a HIV-related condition in a patient, wherein: a low or undetectable viral load is maintained; and/or a CD4+ cell count is stable or increased; after treatment termination.

The invention further relates to uses and methods for treating or preventing a viral infection, in particular HIV infection or a HIV-related condition in a patient in which a decline in a prior anti-retroviral treatment effectiveness has been stated.

The invention further relates to uses and methods for treating or preventing a viral infection, in particular HIV infection or a HIV-related condition in a patient, wherein the patient is infected by a drug-resistant HIV strain.

The invention further relates to uses and methods as defined above, for the preparation of compositions for treating or preventing a viral infection, in particular HIV infection or a HIV-related condition in said patients.

Low Viral Load and Maintained or Restored CD4+ Cell Count after Treatment Termination Viral load is a measure of the severity of a viral infection. Viral load can be used to monitor viral infection, guide treatment, determine the effectiveness of treatment, and predict how a disease caused by the infection may progress. Measurement of viral load is of particular importance for the treatment, prevention and follow-up of viral infections and virus-related conditions.

In the framework of the present invention "maintaining a low viral load after treatment termination" encompasses maintaining a viral load under the detectable level, or alternatively delaying an increase of the viral load by at least two weeks compared to ART and/or HAART treatment.

As used herein the "viral load" also refers to the "viral titer", and it can be determined directly or indirectly. For reference, the viral load generally refers to:
- the number of copies of virus RNA or DNA per mL of a plasma sample;
- the number of virus particles per mL of a plasma sample; and/or
- the activity of a virus-related protein in a plasma sample.

As used herein the "HIV viral load" also refers to the "HIV viral titer", and it can be determined directly or indirectly. For reference, the viral load generally refers to:
- the number of copies of HIV RNA per mL of a plasma sample;
- the number of HIV particles per mL of a plasma sample; and/or
- the activity of a HIV-related protein in a plasma sample, which may for example include determining the reverse transcriptase (RT) activity in said plasma sample.

For reference, methods for determining the HIV viral load in a sample include:
- determining the number of copies of HIV RNA per mL of sample;
- determining the number of HIV particles per mL of sample; and/or
- determining the activity of a HIV-related protein in the sample.

In other words, the viral load remains preferably at an undetectable level at least two weeks after the treatment termination, compared to ART or HAART treatment, which includes at least three, four, or five weeks after the treatment termination.

The HIV viral load test is used primarily to monitor HIV infection over time. It is generally a quantitative measurement of HIV nucleic acid (RNA) that reports how many copies of the virus are present in the blood.

Preferably, and as used herein, the "HIV viral load" relates to the number of copies of HIV RNA per mL of blood plasma. It is generally expressed in HIV RNA copies per mL of blood plasma, according to known methods, which includes nucleic acid-based tests such as reverse-transcriptase polymerase chain reaction (RT-PCR), branched DNA (bDNA), or nucleic acid sequence-based amplification (NASBA) analysis.

In general, a HIV viral load test is ordered when a person is first diagnosed. The test results function as a baseline measurement that shows how actively the virus is reproducing. The HIV viral load test is then performed over time and compared to said baseline measurement or to a reference value, in order to assess a relative variation of the HIV viral load.

Accordingly, conventional methods for determining HIV viral load include:
(i) providing a whole blood sample obtained from a patient;
(ii) removing cells from the sample by centrifugation to provide plasma;
(iii) determining the number of copies of HIV RNA per milliliter of plasma, for example, by reverse-transcriptase polymerase chain reaction (RT-PCR), branched DNA (bDNA), or nucleic acid sequence-based amplification (NASBA) analysis.
(iv) optionally comparing the result obtained at step (iii) with a reference value and/or a baseline measurement.

If a subject has a high HIV viral load (for example, at least 1,000 copies/ml plasma), this may indicate treatment failure, i.e. that the virus is replicating and the disease may progress more quickly. If HIV viral load is low (for example, below 500 copies/mL of plasma), this indicates that the anti-viral treatment regimen is effective, i.e. that the virus may not be actively replicating and the disease may progress more slowly or even be cured.

A low viral load is usually below 500 copies/mL of plasma; which includes between 20 and 500 copies/mL of plasma, or 40 to 500 copies/mL of plasma, depending on the type and sensitivity of the test that is used. This result indicates that HIV is not actively reproducing and that the risk of disease progression is low.

A low viral load may consist of a viral load below 500 copies/mL; which includes below 450, 400, 350, 300, 250, 200, 150, 100, 50, 40, 30, 20, 10, 9, 8, 7, 6, 5, 4, 3, 2, and 1 copies/mL.

An undetectable viral load for routine methods is generally below 40 copies/mL of plasma, which includes 20 copies/mL of plasma, in particular when measured with a method and/or kits selected from: COBAS® AmpliPrep/COBAS® TaqMan® HIV-1 Test and COBAS® AMPLICOR HIV-1 MONITOR Test sold by Roche Molecular Diagnostic or NucliSENS EasyQ®HIV-1 sold by Biomerieux Diagnostics.

However, an undetectable viral load in a patient with diagnosed HIV infection does not mean that the patient is cured; it means only that the level of HIV RNA is currently below the threshold needed for detection. What is more, an undetectable viral load does not necessarily rule out the presence of HIV in latent reservoirs.

Changes in viral load are generally more important during HIV monitoring than obtaining a single test result. An increasing viral load indicates either that the infection is getting worse or that the virus has developed resistance to the drugs that are being used for therapy and are no longer effective. A decreasing viral load indicates improvement, treatment effectiveness, and decrease of the HIV infection.

More particularly, according to this aspect, the invention relates to doses and regimens of a quinoline derivative of formula (I) in the treatment or prevention of virus infections or virus-related conditions in patients, in particular of HIV infection, wherein the viral load after treatment termination is maintained low.

This means that the quinoline derivative of formula (I), and more particularly compound 22 or N-glucuronide metabolite as defined above, presents a surprisingly long-lasting therapeutic effect.

The invention furthermore relates to a method for treating or preventing a virus infection or virus-related condition in a patient, including HIV infection, consisting in administering to a patient in need thereof, an effective amount of a quinoline derivative of formula (I) as described above, wherein said method allows to maintain a low viral load after treatment termination.

According to some embodiments, the invention further relates to a method for treating a virus infection or virus-related condition in a patient, including HIV infection, consisting of:
(i) administering to a patient in need thereof an effective amount of a quinoline derivative of formula (I) thereby treating the patient;
(ii) terminating the treatment;
(iii) optionally measuring the viral load and/or the CD4+ cell count in said patient after termination of treatment;
wherein preferably:

a low or undetectable viral load is maintained; and/or a CD4+ cell count is stable or increased; after treatment termination;

(iv) optionally administering again to said patient in need thereof an effective amount of a quinoline derivative of formula (I) if the viral load is not low or undetectable and/or the CD4+ cell count is decreased.

Preferably, the treatment is terminated when: the viral load is low or undetectable; and/or the level of CD4+ cell count is maintained or restored.

For reference, and as previously disclosed, a low viral load is usually below 500 copies/mL of plasma and an undetectable viral load is usually below 40 copies/mL.

For reference, and as previously disclosed, a restored CD4+ cell count may correspond to a physiological (or "normal") CD4+ cell count, which is generally equal or superior to 500 CD4+ cells/mm$^3$ of plasma, and which generally varies between 500 and 1500 CD4+ cells/mm$^3$ of plasma, though it may be lower for some individuals.

Doses and Regimen

The invention further relates to a method for lowering viral load of HIV virus, and/or increasing the CD4+ cell count, wherein the virus causes a chronic viral infection and is resistant to an antiviral drug, the method comprising the step of administering to a host a efficient amount of a quinoline derivative of formula (I) as defined above, in particular at various frequencies, in doses ranging from 25 to 500 mg, in particular 25 to 200 mg, or even from 25 to 300 mg, and for example from 25 to 150 mg.

According to one embodiment, the treatment frequency may be once a day, once every three days, once a week, once every 2 weeks or once every month.

According to a particular embodiment, the treatment is continuous or non continuous.

A "continuous treatment" means a long-term treatment which can be implemented with various administration frequencies, such as once every three days, or once a week, or once every two weeks or once every month.

The treatment period, i.e. when the treatment is non continuous, may vary between 2 weeks and 8 weeks, which includes 2, 3, 4, 5, 6, 7 and 8 weeks.

According to one embodiment, the quinoline derivative of formula (I), or anyone of its pharmaceutically acceptable salts and metabolites, is administered at a dose varying from 25 to 500 mg, in particular varying from 25 to 300 mg, for example varying from 25 to 200 mg, and in particular varying from 25 to 150 mg. Doses ranging from 25 to 500 mg include doses of about 25, 50, 75, 100, and 150 mg.

Said dosages may be adapted depending if the treatment is continuous or non continuous.

All combinations of doses, frequencies and treatment period are encompassed within the scope of the present invention.

According to a particular embodiment, a quinoline derivative of formula (I) according to the present invention, and more particularly compound 22, may be administered at various dosages and regimen and in particular once a day at doses ranging from 25 to 150 mg or every 3 days at doses ranging from 25 to 150 mg as a continuous treatment or during a treatment period.

The treatment period may vary between 2 weeks and 8 weeks, in particular 2 to 5 weeks.

The quinoline derivative may be administered every day, once every three days, once a week, once every two weeks or once every month.

Several examples of doses and regimens are given herein below.

More particularly the invention relates to a dosage and regimen where the quinoline derivative of formula (I) according to the present invention, and more particularly compound 22, is administered at 25 mg every three days during the treatment period or as a continuous treatment.

More particularly the invention relates to a dosage and regimen where the quinoline derivative of formula (I) according to the present invention, and more particularly compound 22, is administered at 25 mg once a day during the treatment period or as a continuous treatment.

More particularly the invention relates to a dosage and regimen where the quinoline derivative of formula (I) according to the present invention, and more particularly compound 22, is administered at 50 mg every three days during the treatment period or as a continuous treatment.

More particularly the invention relates to a dosage and regimen where the quinoline derivative of formula (I) according to the present invention, and more particularly compound 22, is administered at 50 mg once a day during the treatment period or as a continuous treatment.

More particularly the invention relates to a dosage and regimen where the quinoline derivative of formula (I) according to the present invention, and more particularly compound 22, is administered at 75 mg every three days during the treatment period or as a continuous treatment.

More particularly the invention relates to a dosage and regimen where the quinoline derivative of formula (I) according to the present invention, and more particularly compound 22, is administered at 75 mg once a day during the treatment period or as a continuous treatment.

More particularly the invention relates to a dosage and regimen where the quinoline derivative of formula (I) according to the present invention, and more particularly compound 22, is administered at 100 mg every three days during the treatment period or as a continuous treatment.

More particularly the invention relates to a dosage and regimen where the quinoline derivative of formula (I) according to the present invention, and more particularly compound 22, is administered at 100 mg once a day during the treatment period or as a continuous treatment.

More particularly the invention relates to a dosage and regimen where the quinoline derivative of formula (I) according to the present invention, and more particularly compound 22, is administered at 150 mg every three days during the treatment period or as a continuous treatment.

More particularly the invention relates to a dosage and regimen where the quinoline derivative of formula (I) according to the present invention, and more particularly compound 22, is administered at 150 mg once a day during the treatment period or as a continuous treatment.

Therefore, the result of the tests carried out on the compounds disclosed in the present invention show that the quinoline derivatives of formula (I) as defined above may be useful to treat patients infected by HIV, for which a decline in a prior anti-HIV treatment effectiveness has been stated.

The results further show that the quinoline derivatives of formula (I) as defined above may be useful for a long-lasting low or undetectable viral load and/or maintained or increased CD4+ cell count after treatment termination.

The results further show that the quinoline derivatives of formula (I) as defined above may be suitable for long-term treatment due to the absence of induced HIV strains in the treated patients.

Thus, a compound according to the present invention may be implemented within pharmaceutical composition that may contain an effective amount of said compound, and one or more pharmaceutical excipients.

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions.

Any route of administration may be used. For example, a compound of formula (I) can be administered by oral, parenteral, intravenous, transdermal, intramuscular, rectal, sublingual, mucosal, nasal, or other means. In addition, a compound of formula (I) can be administered in a form of pharmaceutical composition and/or unit dosage form.

In particular, pharmaceutical compositions of the invention may be administered orally and/or parenterally.

According to one exemplary embodiment, pharmaceutical compositions of the invention may be administered orally.

Suitable dosage forms include, but are not limited to, capsules, tablets (including rapid dissolving and delayed release tablets), powder, syrups, oral suspensions and solutions for parenteral administration, and are more particularly capsules.

The pharmaceutical composition may also contain another drug for the treatment of HIV, well known to the man skilled in the art, in combination with a compound according to the present invention.

Advantageously, the compound of formula (I), or anyone of its pharmaceutically acceptable salts and metabolites thereof, may be administered in combination with one or more antiretroviral compounds, including ART and HAART treatments, such as the ones selected from: Zidovudine, Lamivudine, Emtricitabine, Didanosine, Stavudine, Abacavir, Zalcitabine, Tenofivir, Racivir, Amdoxovir, Apricitabine, Elvucitabine, Efavirenz, Nevirapine, Etravirine, Delavirdine, Rilpvirine, Tenofovir, Fosalvudine, Amprenavir, Tipranavir, Indinavir, Saquinavir, Fosamprenavir, Ritonavir, Darunavir, Atazanavir, Nelfinavir, Lopinavir, Raltegravir, Elvitegravir, Dolutegravir, Enfuvirtide, Maraviroc, Vicriviroc, and combinations thereof.

EXAMPLES

Example 1: Potency of Compound 22 and its N-Glucuronide Metabolite to Inhibit HIV-1 Production in PBMC- and Macrophages-Infected Cells 1. Material & Methods A. Cell Culture and Infection Buffy coats from HIV-negative individuals were obtained from the local blood donation center in Zurich, Switzerland (http://www.blutspendezurich.ch/) and Centre de transfusion sanguine Montpellier. Human peripheral blood mononuclear cells (PBMCs) were isolated by Ficoll (Axis-Shield PoC AS) gradient centrifugation. The cells have then been cultivated at 37° C., 5% CO2 to a density of 1×106 cells/mL in RPMI Glutamax medium (Life Technologies Ref 61870-010) supplemented with 10% fetal calf serum (FCS) (Thermo Fischer Ref SV30160.03), 1000 U/mL of IL2 (Peprotech Ref 200-02) and 5 µg/mL of PHA (Roche Ref 1249738) for activation. Three days later, cells have been pooled and resuspended to a density of 1×106 cells/mL in RPMI Glutamax medium supplemented with 10% fetal calf serum (FCS) 1000 U/mL of IL-2 for infection. HIV-1 infection has been performed with 10 µg of Ada-M R5 HIV strain per mL of cells for 4 hours. Cells were then centrifuged and resuspended to a density of 1×106 cells/mL in medium supplemented with diluted DMSO solubilized drug (Sigma Ref D4818) according to a final 0.05% DMSO concentration. Cells were treated for 6 days with a partial medium change at day 3. Cell culture supernatant HIV p24 titration was performed by ELISA with Ingen Innotest kit (Ingen Ref 80564) according to manufacturer's instructions.

To generate monocyte derived macrophages (MDMs), monocytes were isolated using CD14 microbeads (catalog no. 130-050-201; Miltenyi) and cultured in X-VIVO10 medium (Lonza) supplemented with GM-CSF 1000 U/ml and M-CSF 100 ng/ml for 6 days. Monocytes were seeded at a cell count of 50,000 cells per well in a 96 well plate. After 6 days medium was replaced with X-VIVO10 w/o Cytokines. After 2 days Macrophages were treated with Compound 22 and/or its N-glucuronide metabolite o/n and next day infected with Yu-2 virus for 6 hrs, washed with PBS and cultured in medium containing the compounds for 12 days. Supernatant for p24 Elisa was collected 2 times a week.

B. Monitoring of p24 Antigen Levels.

Cells were treated with 0.01 µM up to 30 µM and p24 antigen levels were monitored in culture supernatant over a 12 day period. Cell culture supernatant HIV p24 titration was performed by ELISA with Ingen Innotest kit (Ingen Ref 80564) according to the manufacturer's instructions.

2. Results

The first functional study was based on the use of freshly isolated human peripheral blood mononuclear cells (PBMCs) from healthy donors. These PBMCs were infected by the laboratory HIV strain Ada-MRS.

FIG. 1A shows dose dependent inhibition of HIV-1 replication in stimulated PBMCs from 7 different donors. Interestingly, treatment with Compound 22 did not alter the different populations of lymphocytes present in PBMCs.

To generalize the effect of Compound 22 on HIV-1 replication in other primary cells, the same protocol was repeated using infected macrophages, which act as viral reservoirs. Cells were treated with 0.01 µM up to 30 µM and p24 antigen levels were monitored in culture supernatant over a 12 day period (FIG. 1B).

The effect of the N-glucuronide metabolite on p24 inhibition and HIV replication on macrophages infected with Yu-2 virus has also been shown for concentrations of 1.5 µM, 10 µM and 30 µM. Interestingly, Compound 22 and its N-glucuronide metabolite blocked virus replication efficiently and in a dose dependent manner reaching inhibition levels of up to 90% in primary macrophages at 0.1 µM. However, cell viability was not decreased under Compound 22 treatment (data not shown).

Those Results Provide Evidence that the Compounds of the Invention have Low Toxicity, but Remain Suitable for Inhibiting HIV-1 Replication, in PBMCs and Macrophages.

Since the previous experiments were all performed with primary human cells infected with macrophage-tropic (R5) strains (Ada-MR5 and YU2), we shifted to an in vitro system that may be more relevant to the clinical situation since it involves infecting primary cells with HIV-1 isolates from patients. As shown in FIG. 2A, Compound 22 had a strong inhibitory effect for all HIV-1 subtypes tested including subtype B, C and recombinant viruses. In particular, Compound 22 very efficiently inhibits the replication of viral strains harbouring mutations that confer resistance to different therapeutic agents in vitro (FIG. 2B), and there were no resistance-inducing mutations detected after treatment with Compound 22 for at least 24 weeks, as further evidence herebelow:

To test for emergence and/or selection of mutations associated with Compound 22 treatment, we applied a deep sequencing approach for sensitive detection of low-frequency viral variants across the entire HIV-1 genome. Viruses derived from treated and untreated infected primary macrophages of 4 different donors were sequenced and reads not aligning to human genome were aligned to YU2 sequence using gsnap, as detailed in Wu et al. (Fast and SNP-tolerant detection of complex variants and splicing in short reads. Bioinformatics 26, 873-881 (2010)). The majority of low and high frequency mutations were equally present in treated and untreated samples demonstrating that Compound 22 does not select for specific mutations.

To ascertain that amplification of viruses from treated samples will not mutate when amplified in PBMCs, they were sequenced following amplification with or without drug pressure.

Again, no novel mutations were detected other than the ones existing before treatment in the original samples. We conclude that Compound 22 is unlikely to select for specific viral mutations. Furthermore, Compound 22 also very efficiently inhibits the replication of viral strains harbouring mutations that confer resistance to different therapeutic agents in vitro and there were no resistance-inducing mutations detected after treatment with Compound 22 for at least 24 weeks (Table 1).

Resistance to Compound 22 was tested on human PBMCs and compared to current therapies. There were no resistance-inducing mutations detected after treatment with Compound 22 for at least 24 weeks. Various classes of antiviral agents can affect the life cycle of HIV-1 in different manners. Genetic heterogeneity is a characteristic of this virus, which contributes significantly to its ability to generate mutations that overcome the efficacy of drug therapies. The selection of drug resistant mutants in vitro can be readily accomplished by maintaining the virus in a state of sub-optimal growth, regulated by slowly increasing the amount of drug pressure applied. This technique mimics the consequences of drug therapy in patients. Therefore, in this way, novel compounds can be assessed for their selection profile in order to evaluate the likelihood of emergence of HIV-1 drug resistance in future clinical trials. In addition, combinations of drugs can be investigated in the same manner.

TABLE 1 mutation selection with various drugs on human PBMCs.

| Compound | Starting Concentration | Time of Selection (weeks) | Mutation Selected |
| --- | --- | --- | --- |
| 3TC | 0.05 µM | 4 | M184I/V |
| Tenofovir | 0.05 µM | 12 | K65R |
| Nevirapine | 0.01 µM | 3 | K103N & Y181C |
| Efavirenz | 0.01 µM | 5 | K103N & Y181C |
| Compound 22 | 10 µM | 24 | — |

Those results provide evidence that compound 22 do not select for HIV specific mutations and are not genotoxic.

Example 2: Efficacy of Compound 22 to Inhibit Viral Replication in Humanized Mice 1. Material & Methods
A. Generation of Humanized Mouse Models SCID mice were reconstituted with fresh human PBL for two weeks and the reconstitution rates were estimated by human IgG titration according to Denton et al. (Humanized mouse models of HIV infection. AIDS Rev 13, 135-148 (2011)) and Berges et al. (The utility of the new generation of humanized mice to study HIV-1 infection: transmission, prevention, pathogenesis, and treatment. Retrovirology 8, 65 (2011)).

Reconstituted SCID mice were infected with JRCSF HIV-1 strain by intraperitoneal injection. Control group received by gavage labrafil and 5% DMSO (n=15) and treated group 20 mg/kg b.i.d of Compound 22 in labrafil and 5% DMSO (n=14) for 15 days.

NOD.scid.IL2R−/− (NSG) mice were bred and maintained in individual ventilated cages and were fed autoclaved food and water. Mice with a human immune system (NSG-HIS) were generated as described in Nischang et al. (Humanized mice recapitulate key features of HIV-1 infection: a novel concept using long-acting anti-retroviral drugs for treating HIV-1. PLoS ONE 7, e38853 (2012).

Briefly, newborn (<5 days old) NSG mice received sublethal (1Gy) total body irradiation with a Cs source, and then received 2×105 transduced or untransduced CD34+ human HSCs using a 50 µl Hamilton syringe via the intrahepatic (i.h.) route. All manipulations of NSG-HIS mice were performed under laminar flow. Gavage of mice was performed daily with a stainless steel gavage needle (Straight 22 Gauge, 1.4 inch in length). Compound 22 was dissolved in DMSO (Sigma), and then diluted to 5% or less according to the dose required in a suitable vehicle (Labrafil M 1944 CS; COOPER INDUSTRIE, Place Lucien Auvert 77020 MELUN CEDEX 20). Mice did not receive more than 150 µl in volume per day. Mice were monitored three times a week for symptoms or signs of adverse events, according to a standard score sheet.

B. HIV Virus Stock and Infection of Mice

JR-CSF viral stocks were amplified in PBMCs, virus was harvested after 12 to 15 days post-infection, filtered (0.45 µm), concentrate by centrifugation on a sucrose cushion and frozen at −80° C. YU-2 viral stocks were obtained by polyethylenimine (PEI)-mediated transfection (Polysciences) of 293T cells with a pYU-2 (R5 tropic) plasmid provided through the NIH AIDS Research and Reference Reagent Program. 48 hours after transfection, the virus was harvested, filtered (0.45 µm), and frozen at −80° C. Viral titers were determined as described in McDougal et al. (Immunoassay for the detection and quantitation of infectious human retrovirus, lymphadenopathy-associated virus (LAV). J. Immunol. Methods 76, 171-183 (1985)).

Briefly, TCID50 (tissue culture infectious dose 50%) was determined by infecting human CD8+ T-cell-depleted peripheral blood mononuclear cells (PBMCs) from three donors which were stimulated by addition of IL-2, PHA and anti-CD3 beads (Dynal 11131D, Life Technologies). Then, viral stocks were adjusted to 1×10$^6$ TCID50/ml, aliquoted and frozen at −80° C. before use. Mice were infected intraperitoneally i.p. with JR-CSF, 1×10$^3$ TCID50 per mouse and HIV YU-2, 1×106 TCID50 per mouse. HIV RNA plasma levels were measured by RT-PCR (Amplicor HIV-1 test or AmpliPrep/COBAS TaqMan HIV-1 Test, Roche) at various times after infection.

C. Flow Cytometry

Cell suspensions were labeled with anti-human monoclonal antibodies (mAb) targeting the following cell-surface markers: CD45-FITC, CD3-PE, CD4-Pe Cy7, CD8-BV421 and CD19-APC (all from Biolegend). Washing and reagent dilutions were done with FACS buffer (PBS containing 2% fetal calf serum and 0.05% sodium azide (NaN3). All acquisitions were performed on a Cyan ADP (Beckman Coulter) flow cytometer. Data were analyzed with FlowJo software (Ashland, Oreg.). Cellular debris and dead cells were excluded by their light-scattering characteristics.

2. Results

Humanized mice reconstituted with human lymphoid cells, provide rapid, reliable, reproducible experimental systems for testing the efficacy of Compound 22 in vivo. In the initial setting, SCID mice were reconstituted with PBMCs and then infected with the HIV-1 strain JR-CSF. Mice were treated by oral gavage with Compound 22 at a dose-level of 20 mg/kg twice a day for 15 days. Measures of viral RNA showed that oral treatment with Compound 22 was able to significantly reduce the viral load over a period of 15 days of treatment (FIG. 3A). FACS analysis of blood samples showed that treatment with Compound 22 prevents depletion of CD4+ cells following infection of reconstituted mice and thereby restores CD8+/CD4+ ratio back to that of non-infected mice (FIG. 3B).

Figure 3D:
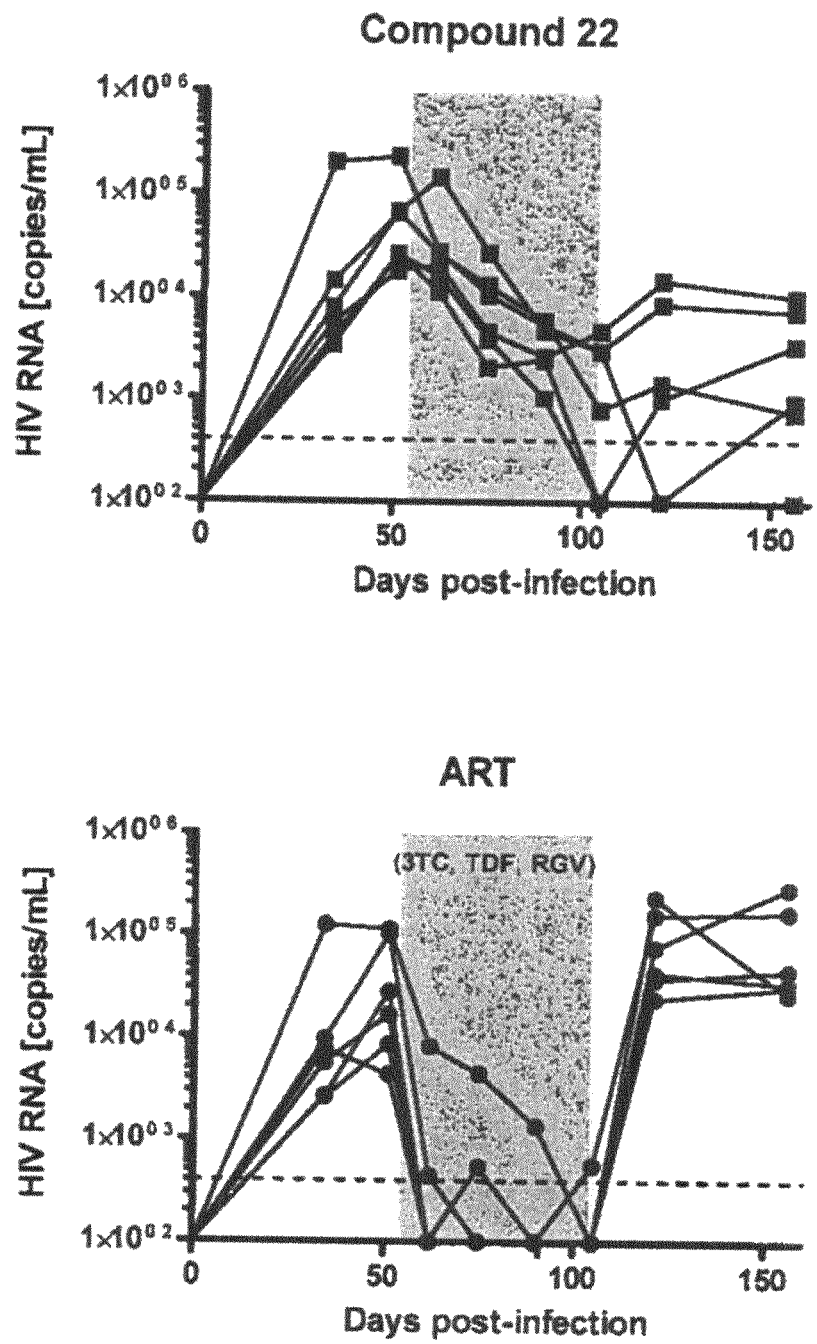

To test the long term effect of Compound 22 on the immune system and viral replication in infected hu mice, newborn NOG mice were transplanted with CD34+ haematopoietic progenitor cells isolated from umbilical cord blood (see Nischang et al.; Humanized mice recapitulate key features of HIV-1 infection: a novel concept using long-acting anti-retroviral drugs for treating HIV-1. PLoS ONE 7, e38853; 2012). This hu mouse model has previously been shown to be valuable for exploring the antiviral potency of new compounds targeting the latent HIV reservoirs. Treatment of NOG hu mice for one month with 20 mg/kg or 40 mg/kg of Compound 22 neither alters engraftment values of CD45+ cells nor the ratio of CD8+/CD4+ compared to controls without treatment (FIG. 3C). In this study NOG hu mice were infected with the YU2 HIV-1 virus and fed daily for 30 days with 40 mg/kg of Compound 22 or with HAART (3TC-Tenofovir-Raltegravir and AZT) and viral loads were measured as before. Compound 22 reduced the viral load over a period of 30 days of treatment but more importantly, the viral load remained low for at least 50 days after treatment termination (FIG. 3D). In contrast, rebound up to levels comparable to the initial infection was seen in the HAART group (FIG. 3D).

Thus those results show that Compound 22 is the first robust anti-HIV drug able to suppress viral load sustainably after treatment arrest.

Example 3: Compound 22 Increases the Levels of Spliced HIV RNA

1. Material & Methods

A. Quantification of Viral and Non-Viral RNA Splicing

Quantification of viral RNA splicing is achieved using the protocols detailed in Bakkour et al. (Small-molecule inhibition of HIV pre-mRNA splicing as a novel antiretroviral therapy to overcome drug resistance. PLoS Pathog. 3, 1530-1539 (2007).

Quantification of non-viral RNA splicing is achieved using the protocols detailed in Klinck et al. (Multiple alternative splicing markers for ovarian cancer. *Cancer Res.* 68, 657-663 (2008)) and Venables et al. (Cancer-associated regulation of alternative splicing. *Nat. Struct. Mol. Biol.* 16, 670-676 (2009)).

Other protocols are as described previously.

2. Results

In order to verify that Compound 22 does not significantly affect the splicing events of endogenous genes, which could potentially lead to some adverse effects, the effect of Compound 22 was tested by RT-PCR analysis of global alternative splicing on 382 alternative splicing events. These 382 alternative splicing events (ASEs) represent a high throughput random snapshot of global alterations of alternative splicing. We performed high throughput PCR analysis of these (essentially random) 382 ASEs on multiple PBMC samples, either from untreated (cells) or treated with DMSO, Compound 22 or with the control antiviral drug (Darunavir). Analysis of the data allowed further stringent quality controls; ASEs were only considered if >75% of the products ran at the expected mobilities (i.e. if the reactions were pure) and if total expected PCR concentration was higher than 20 nM (i.e. if the reactions were strong) which led to 264 remaining ASEs.

The splicing profiles of 12 PBMC samples from the same donor show that there is very little difference in the splicing profiles of the drug-treated PBMC samples as they form one of three separate poles with the stem cells and their derived fibroblasts. Consistent with this, the untreated cells and Compound 22 treated cells percent spliced in values for these 264 ASEs had a correlation of R=0.89, whereas stem cells and derived fibroblasts only correlated at R=0.59 (data not shown). Taken together, these data show that Compound 22 has no global effect on pre-mRNA splicing.

To test whether Compound 22 influences the splicing of HIV RNA in infected cells, an array-based sequence capture was performed using a customized library probes targeting HIV sequences to get rid of cellular RNA. The probes were used to capture cDNAs prepared from infected treated and untreated PBMCs. After double capture, libraries were prepared and sequenced using 454 pyrosequencing (according to GS junior method manual). The average size of the reads around 400 bp allowed unambiguous assembly of viral genome from untreated sample (after 3 and 6 days of infection) using reads that were not mapped to human genome (hg19). All sequencing data were analysed using gsnap, as detailed in Wu et al. (Fast and SNP-tolerant detection of complex variants and splicing in short reads. Bioinformatics 26, 873-881 (2010)).

After 3 days post infection a higher coverage of viral genome was obtained for the untreated DMSO sample (32,289 reads) compared to Compound 22 treated sample (4149 reads). Strikingly, at 3 days post-infection 17.4% of the reads from treated sample corresponded to splice junctions, against 0.93% in the untreated sample. While the number of reads from treated and untreated samples were similar at 6 days post-infection (20 585 and 27 984, respectively), the fraction corresponding to splice junctions was again larger in treated (13.3%) compared to untreated sample (1.93%).

Based on these results it can be concluded that Compound 22 favours spliced HIV RNA in infected PBMCs, thereby compromising subsequent synthesis of full-length HIV-1 pre-mRNA and assembly of infectious particles.

The invention claimed is:

1. A method of treating or reducing the likelihood of occurrence or reducing the likelihood of reoccurrence of a human immunodeficiency virus (HIV) infection or an AIDS condition for which an ineffectiveness or a decline in a prior anti-viral treatment effectiveness has been stated, the method comprising administering a quinoline derivative of formula (I)

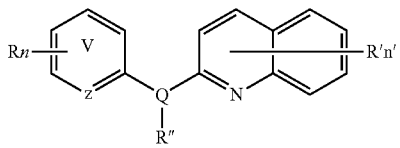

wherein:

z represents N or C,

means an aromatic ring wherein V is C or N and when V is N, V is in ortho, meta or para of z, R independently represent a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a (C$_3$-C$_6$)cycloalkyl group, a —NO$_2$ group, a —NR$_1$R$_2$ group, a (C$_1$-C$_4$)alkoxy group, a phenoxy group, a —NR$_1$—SO$_2$—NR$_1$R$_2$ group, a —NR$_1$—SO$_2$—R$_1$ group, a —NR$_1$—C(=O)—R$_1$ group, a —NR$_1$—C(=O)—NR$_1$R$_2$ group, a —SO$_2$—NR$_1$R$_2$ group, a —SO$_3$H group, a —O—SO$_2$—OR$_3$ group, a —O—P(=O)—(OR$_3$)(OR$_4$) group, a —O—CH$_2$—COOR$_3$ group and a (C$_1$-C$_3$)alkyl group, said alkyl being optionally monosubstituted by a hydroxyl group, Q is N or O, provided that R" does not exist when Q is O, R$_1$ and R$_2$ are independently a hydrogen atom or a (C$_1$-C$_3$)alkyl group, R$_3$ and R$_4$ independently represent a hydrogen atom, Li$^+$, Na$^+$, K$^+$, N$^+$(Ra)$_4$ or a benzyl group, n is 1, 2 or 3, n' is 1, 2 or 3, R' independently represent a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$)alkoxy group and a —CN group, and can further be a group chosen among:

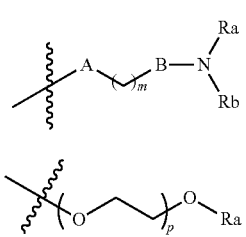

A is a covalent bond, an oxygen atom or NH,
B is a covalent bond or NH, m is 1, 2, 3, 4 or 5, p is 1, 2 or 3, Ra and Rb independently represent a hydrogen atom, a (C$_1$-C$_5$)alkyl group or a (C$_3$-C$_6$)cycloalkyl group, Ra and Rb can further form together with the nitrogen atom to which they are attached a saturated 5- or 6-membered heterocycle optionally containing a further heteroatom chosen among N, O and S, said heterocycle being optionally substituted by one or more Ra, provided that when R' is a group (IIa) or (IIIa), n' may be 2 or 3 only if other R' groups are different from said group (IIa) or (IIIa), R" is a hydrogen atom, a (C$_1$-C$_4$)alkyl group or is a group (IIa) as defined above, or any one of its pharmaceutically acceptable salts.

2. The method of claim 1, wherein the patient has an increased HIV viral load.

3. The method of claim 1, wherein said quinoline derivative, is administered once every month at doses varying from 25 to 500 mg during a treatment period or as a continuous treatment.

4. The method of claim 1, wherein the treatment period varies from 2 to 8 weeks.

5. The method of claim 1, wherein said quinoline derivative has the following formula (Ib)

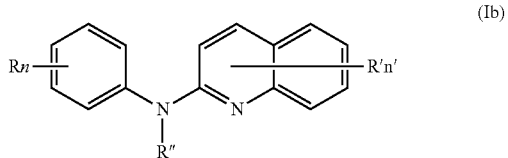

wherein R, R', R", n and n' are as defined in claim 1, or anyone of its pharmaceutically acceptable salt.

6. The method of claim 1, wherein the quinoline derivative is 8-chloro-N-(4-(trifluoromethoxy)phenyl)quinolin-2-amine.

7. The method according to claim 1, which is for reducing the likelihood of occurrence or reducing the likelihood of reoccurrence of a human immunodeficiency virus (HIV) infection or a AIDS condition.

8. A method of treating or reducing the likelihood of occurrence or reducing the likelihood of reoccurrence of a human immunodeficiency virus (HIV) infection or an AIDS condition in a patient infected by an AIDS strain that is resistant to ART or HAART treatment, or by a HIV strain that is resistant to a drug selected from: Zidovudine, Lamivudine, Emtricitabine, Didanosine, Stavudine, Abacavir, Zalcitabine, Tenofivir, Racivir, Amdoxovir, Apricitabine, Elvucitabine, Efavirenz, Nevirapine, Etravirine, Delavirdine, Rilpvirine, Tenofovir, Fosalvudine, Amprenavir, Tipranavir, Indinavir, Saquinavir, Fosamprenavir, Ritonavir, Darunavir, Atazanavir, Nelfinavir, Lopinavir, Raltegravir, Elvitegravir, Dolutegravir, Enfuvirtide, Maraviroc, Vicriviroc, and combinations thereof, the method comprising administering to the patient a quinoline derivative of formula (I)

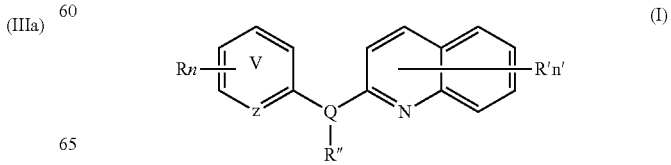

wherein:

z represents N or C,

means an aromatic ring wherein V is C or N and when V is N, V is in ortho, meta or para of z, R independently represent a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a (C$_3$-C$_6$) cycloalkyl group, a —NO$_2$ group, a —NR$_1$R$_2$ group, a (C$_1$-C$_4$)alkoxy group, a phenoxy group, a —NR$_1$—SO$_2$—NR$_1$R$_2$ group, a —NR$_1$—SO$_2$—R$_1$ group, a —NR$_1$—C(=O)—R$_1$ group, a —NR$_1$—C(=O)—NR$_1$R$_2$ group, a —SO$_2$—NR$_1$R$_2$ group, a —SO$_3$H group, a —O—SO$_2$—OR$_3$ group, a —O—P(=O)—(OR$_3$)(OR$_4$) group, a —O—CH$_2$—COOR$_3$ group and a (C$_1$-C$_3$)alkyl group, said alkyl being optionally monosubstituted by a hydroxyl group, Q is N or O, provided that R″ does not exist when Q is O, R$_1$ and R$_2$ are independently a hydrogen atom or a (C$_1$-C$_3$)alkyl group, R$_3$ and R$_4$ independently represent a hydrogen atom, Li$^+$, Na$^+$, K$^+$, N$^+$(Ra)$_4$ or a benzyl group, n is 1, 2 or 3, n' is 1, 2 or 3, R' independently represent a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$)alkoxy group and a —CN group, and can further be a group chosen among:

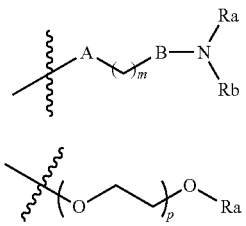

(IIa)

(IIIa)

A is a covalent bond, an oxygen atom or NH,

B is a covalent bond or NH, m is 1, 2, 3, 4 or 5, p is 1, 2 or 3,

Ra and Rb independently represent a hydrogen atom, a (C$_1$-C$_5$)alkyl group or a (C$_3$-C$_6$)cycloalkyl group, Ra and Rb can further form together with the nitrogen atom to which they are attached a saturated 5- or 6-membered heterocycle optionally containing a further heteroatom chosen among N, O and S, said heterocycle being optionally substituted by one or more Ra, provided that when R' is a group (IIa) or (IIIa), n' may be 2 or 3 only if other R' groups are different from said group (IIa) or (IIIa), R″ is a hydrogen atom, a (C$_1$-C$_4$)alkyl group or is a group (IIa) as defined above, or any one of its pharmaceutically acceptable salts.

9. The method of claim 8, wherein the drug resistant viral strain is a drug-resistant HIV strain that is resistant to a drug selected from ART and/or HAART treatment.

10. The method of claim 8, wherein the drug resistant viral strain is a drug-resistant HIV strain that is resistant to a drug selected from: Zidovudine, Lamivudine, Emtricitabine, Didanosine, Stavudine, Abacavir, Zalcitabine, Tenofivir, Racivir, Amdoxovir, Apricitabine, Elvucitabine, Efavirenz, Nevirapine, Etravirine, Delavirdine, Rilpvirine, Tenofovir, Fosalvudine, Amprenavir, Tipranavir, Indinavir, Saquinavir, Fosamprenavir, Ritonavir, Darunavir, Atazanavir, Nelfinavir, Lopinavir, Raltegravir, Elvitegravir, Dolutegravir, Enfuvirtide, Maraviroc, Vicriviroc, and combinations thereof.

11. The method of claim 8, wherein the patient has not previously been treated by an anti-HIV treatment.

12. The method according to claim 8, which is for reducing the likelihood of occurrence or reducing the likelihood of reoccurrence of a human immunodeficiency virus (HIV) infection or a AIDS condition.

13. A method of treating or reducing the likelihood of occurrence or reducing the likelihood of reoccurrence of a human immunodeficiency virus (HIV) infection or an AIDS condition, the method comprising at least the steps of:

a) administering to a patient a quinolone derivative of formula (I)

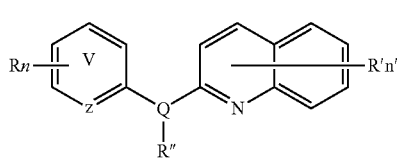

(I)

wherein:

z represents N or C,

means an aromatic ring wherein V is C or N and when V is N, V is in ortho, meta or para of z, R independently represent a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a (C$_3$-C$_6$) cycloalkyl group, a —NO$_2$ group, a —NR$_1$R$_2$ group, a (C$_1$-C$_4$)alkoxy group, a phenoxy group, a —NR$_1$—SO$_2$—NR$_1$R$_2$ group, a —NR$_1$—SO$_2$—R$_1$ group, a —NR$_1$—C(=O)—R$_1$ group, a —NR$_1$—C(=O)—NR$_1$R$_2$ group, a —SO$_2$—NR$_1$R$_2$ group, a —SO$_3$H group, a —O—SO$_2$—OR$_3$ group, a —O—P(=O)—(OR$_3$)(OR$_4$) group, a —O—CH$_2$—COOR$_3$ group and a (C$_1$-C$_3$)alkyl group, said alkyl being optionally monosubstituted by a hydroxyl group, Q is N or O, provided that R″ does not exist when Q is O, R$_1$ and R$_2$ are independently a hydrogen atom or a (C$_1$-C$_3$)alkyl group, R$_3$ and R$_4$ independently represent a hydrogen atom, Li$^+$, Na$^+$, K$^+$, N$^+$(Ra)$_4$ or a benzyl group, n is 1, 2 or 3,
n' is 1, 2 or 3,
R' independently represent a hydrogen atom or a group chosen among a $(C_1-C_3)$alkyl group, a halogen atom, a hydroxyl group, a —$COOR_1$ group, a —$NO_2$ group, a —$NR_1R_2$ group, a morpholinyl or a morpholino group, a N-methylpiperazinyl group, a $(C_1-C_3)$fluoroalkyl group, a $(C_1-C_4)$alkoxy group and a —CN group, and can further be a group chosen among:

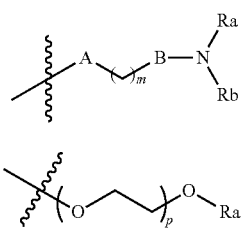

(IIa)

(IIIa)

A is a covalent bond, an oxygen atom or NH,
B is a covalent bond or NH,
m is 1, 2, 3, 4 or 5,
p is 1, 2 or 3, Ra and Rb independently represent a hydrogen atom, a $(C_1-C_5)$alkyl group or a $(C_3-C_6)$cycloalkyl group, Ra and Rb can further form together with the nitrogen atom to which they are attached a saturated 5- or 6-membered heterocycle optionally containing a further heteroatom chosen among N, O and S, said heterocycle being optionally substituted by one or more Ra, provided that when R' is a group (IIa) or (IIIa), n' may be 2 or 3 only if other R' groups are different from said group (IIa) or (IIIa), R" is a hydrogen atom, a $(C_1-C_4)$alkyl group or is a group (IIa) as defined above, or any one of its pharmaceutically acceptable salts, and b) terminating said administration when the HIV viral load in said patient is low or undetectable, and/or the level of CD4+ cell count is maintained or restored.

14. The method of claim 13, wherein the HIV viral load is low if below 500 copies/m of plasma, the HIV viral low is undetectable if below 40 copies/mL of plasma, and the level of CD4+ cell count is restored if equal or superior to 500 CD4+ cells/mm$^3$ of plasma.

15. The method according to claim 13, which is for reducing the likelihood of occurrence or reducing the likelihood of reoccurrence of a human immunodeficiency virus (HIV) infection or a AIDS condition.

* * * * *